(12) United States Patent
Dorsch et al.

(10) Patent No.: US 7,872,039 B2
(45) Date of Patent: Jan. 18, 2011

(54) 3-AMINOINDAZOLES

(75) Inventors: Dieter Dorsch, Ober-Ramstadt (DE); Lars Thore Burgdorf, Frankfurt am Main (DE); Rolf Gericke, Seeheim-Jugenheim (DE); Norbert Beier, Reinheim (DE); Werner Mederski, Zwingenberg (DE); Florian Lang, Tuebingen (DE)

(73) Assignee: Merck Patent Gesellschaft, Darmstadt (DE)

( * ) Notice: Subject to any disclaimer, the term of this patent is extended or adjusted under 35 U.S.C. 154(b) by 380 days.

(21) Appl. No.: 11/629,504

(22) PCT Filed: Apr. 4, 2005

(86) PCT No.: PCT/EP2005/003513

§ 371 (c)(1),
(2), (4) Date: Dec. 14, 2006

(87) PCT Pub. No.: WO2005/123688

PCT Pub. Date: Dec. 29, 2005

(65) Prior Publication Data

US 2007/0232620 A1    Oct. 4, 2007

(30) Foreign Application Priority Data

Jun. 15, 2004    (DE) ................ 10 2004 028 862

(51) Int. Cl.
*A01N 43/56* (2006.01)
*A61K 31/415* (2006.01)
*C07D 231/56* (2006.01)

(52) U.S. Cl. .................... 514/407; 548/362.1

(58) Field of Classification Search ........... 514/407; 548/362.1
See application file for complete search history.

(56) References Cited

U.S. PATENT DOCUMENTS

| | | | | |
|---|---|---|---|---|
| 2,971,842 | A * | 2/1961 | Moore et al. | 430/155 |
| 2,996,467 | A * | 8/1961 | Hawley et al. | 524/60 |
| 7,297,709 | B2 * | 11/2007 | Dai et al. | 514/406 |
| 2004/0110956 | A1 * | 6/2004 | Lesuisse et al. | 546/275.7 |

FOREIGN PATENT DOCUMENTS

| | | | |
|---|---|---|---|
| DE | 12 80 878 B | | 10/1968 |
| WO | WO 02/22601 | * | 3/2002 |
| WO | WO 02/096873 | * | 12/2002 |
| WO | WO 03/051847 | * | 6/2003 |
| WO | WO 03/064397 | * | 8/2003 |
| WO | WO 03/097610 | * | 11/2003 |
| WO | WO 03/097610 A | | 11/2003 |
| WO | WO 2004/022544 A | | 3/2004 |
| WO | WO 2004/112719 | * | 12/2004 |
| WO | WO 2004/113303 | * | 12/2004 |
| WO | WO 2004/113304 | * | 12/2004 |
| WO | WO 2005/011681 A | | 2/2005 |

OTHER PUBLICATIONS

West, Anthony R., Solid State Chemistry and Its Applications, Wiley, New York, 1988, 358.*
Boehmer, et al., Post-translational Regulation of EAAT2 Function by Co-expressed Ubiquitin Ligase Nedd4-2 Is Impacted by SGK Kinases, J. of Neurochem., 97, 911-921 (2006).*
Vippagunta et. al., Advanced Drug Delivery Reviews 48 (2001) 3-26.*
Maren Hertweck et al., C. Elegans SGK-1 Is the Critical Component in The AKT/PKB Kinase Complex to Control Stress Response And Life Span, Developmental Cell, Apr. 2004, pp. 577-588, vol. 6, Cell Press.
Polymorphism: in the pharmaceutical industry (edited by Ralf Hilfker; 2006 Wiley-VCH), Chapter 8, The Importance of Solvates, by U. J. Griesser, pp. 211-222 (hereinafter Griesser).

* cited by examiner

*Primary Examiner*—James O Wilson
*Assistant Examiner*—Erich A Leeser
(74) *Attorney, Agent, or Firm*—Millen, White, Zelano & Branigan, P.C.

(57) ABSTRACT

Novel 3-aminoindazoles of the formula (I) are SGK inhibitors and can be used for the treatment of SGK-induced diseases and conditions, such as diabetes, obesity, metabolic syndrome (dyslipidaemia), systemic and pulmonary hypertonia, cardiovascular diseases and renal diseases, generally in fibrosis and inflammatory processes of any type.

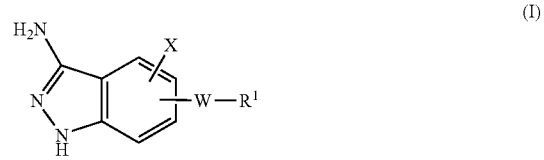

20 Claims, No Drawings

3-AMINOINDAZOLES

BACKGROUND OF THE INVENTION

The invention had the object of finding novel compounds having valuable properties, in particular those which can be used for the preparation of medicaments.

The present invention relates to compounds in which the inhibition, regulation and/or modulation of kinase signal transduction, in particular by the cell volume-regulating human kinase h-sgk (human serum and glucocorticoid dependent kinase or SGK), plays a role, furthermore to pharmaceutical compositions which comprise these compounds, and to the use of the compounds for the treatment of SGK-induced diseases.

The SGKs having the isoforms SGK-1, SGK-2 and SGK-3 are a serine/threonine protein kinase family (WO 02/17893).

The compounds according to the invention are preferably selective inhibitors of SGK-1. They may furthermore be inhibitors of SGK-2 and/or SGK-3.

In detail, the present invention relates to compounds which inhibit, regulate and/or modulate signal transduction by SGKs, to compositions which comprise these compounds, and to processes for the use thereof for the treatment of SGM-induced diseases and conditions, such as diabetes (for example diabetes mellitus, diabetic nephropathy, diabetic neuropathy, diabetic angiopathy and microangiopathy), obesity, metabolic syndrome (dyslipidaemia), systemic and pulmonary hypertonia, cardiovascular diseases (for example cardial fibroses after myocardial infarction, cardiac hypertrophy and cardiac insufficiency, arteriosclerosis) and renal diseases (for example glomerulosclerosis, nephrosclerosis, nephritis, nephropathy, electrolyte excretion disorder), generally in any type of fibrosis and inflammatory processes (for example liver cirrhosis, pulmonary fibrosis, fibrosing pancreatitis, rheumatism and arthritis, Crohn's disease, chronic bronchitis, radiation fibrosis, sclerormatitis, cystic fibrosis, scarring, Alzheimer's disease).

The compounds according to the invention can also inhibit the growth of tumour cells and tumour metastases and are therefore suitable for tumour therapy.

The compounds according to the invention are furthermore used for the treatment of coagulopathies, such as, for example, dysfibrinogenaemia, hypoproconvertinaemia, haemophilia B, Stuart-Prower defect, prothrombin complex deficiency, consumption coagulopathy, hyperfibrinolysis, immunocoagulopathy or complex coagulopathies, and also in neuronal excitability, for example epilepsy. The compounds according to the invention can also be employed therapeutically in the treatment of a glaucoma or cataract. The compounds according to the invention are furthermore used in the treatment of bacterial infections and in antiinfection therapy. The compounds according to the invention can also be employed therapeutically for increasing learning ability and attention.

In addition, the compounds according to the invention counter cell ageing and thus increase life expectancy and fitness in the elderly.

The compounds according to the invention are furthermore used in the treatment of tinitus.

The identification of small compounds which specifically inhibit, regulate and/or modulate signal transduction of SGKs is therefore desirable and an aim of the present invention.

It has been found that the compounds according to the invention and salts thereof have very valuable pharmacological properties while being well tolerated.

In particular, they exhibit inhibiting effects on SGK.

The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases and also to a process for the treatment of the said diseases which comprises the administration of one or more compounds according to the invention to a patient in need of such an administration.

The host or patient may belong to any mammal species, for example a primate species, particularly humans; rodents, including mice, rats and hamsters; rabbits; horses, cows, dogs, cats, etc. Animal models are of interest for experimental investigations, where they provide a model for the treatment of a human disease.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascase, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein are described in the literature (for example Campos-González, R. and Glenney, Jr., J. R. 1992, J. Biol. Chem. 267, page 14535).

Various assay systems are available for identification of kinase inhibitors. In the scintillation proximity assay (Sorg et al., J. of. Biomolecular Screening, 2002, 7, 11-19) and the flashplate assay, the radioactive phosphorylation of a protein or peptide as substrate using γATP is measured. In the presence of an inhibitory compound, a reduced radioactive signal, or none at all, is detectable. Furthermore, homogeneous time-resolved fluorescence resonance energy transfer (HTR-FRET) and fluorescence polarisation (FP) technologies are useful as assay methods (Sills et al., J. of Biomolecular Screening, 2002, 191-214).

Other non-radioactive ELISA assay methods use specific phospho anti-bodies (phospho ABs). The phospho AB only binds the phosphorylated substrate. This binding can be detected by chemoluminescence using a second peroxidase-conjugated antisheep antibody (Ross et al., Biochem. J., 2002, 366, 977-981).

PRIOR ART

Other indazole derivatives are described as protein kinase inhibitors in WO 03/064397.

WO 00/62781 describes the use of medicaments comprising inhibitors of cell volume-regulated human kinase H-SGK.

The use of kinase inhibitors in antiinfection therapy is described by C. Doerig in Cell. Mol. Biol. Lett. Vol. 8, No. 2A, 2003, 524-525.

The use of kinase inhibitors in obesity is described by N. Perrotti in J. Biol. Chem. 2001, March 23; 276(12):9406-9412.

The following references suggest and/or describe the use of SGK inhibitors in disease treatment:

1: Chung E J, Sung Y K, Farooq M, Kim Y, Im S, Tak W Y, Hwang Y J, Kim Y I, Han H S, Kim J C, Kim M K. Gene expression profile analysis in human hepatocellular carcinoma by cDNA microarray. Mol. Cells. 2002; 14:382-7.
2: Brickley D R, Mikosz C A, Hagan C R, Conzen S D. Ubiquitin modification of serum and glucocorticoid-induced protein kinase-1(SGK-1). J Biol. Chem. 2002; 277: 43064-70.
3: Fillon S, Klingel K, Warntges S, Sauter M, Gabrysch S, Pestel S, Tanneur V, Waldegger S, Zipfel A, Viebahn R, Haussinger D, Broer S, Kandolf R, Lang F. Expression of the serine/threonine kinase hSGK1 in chronic viral hepatitis. Cell Physiol Biochem. 2002; 12:47-54.
4: Brunet A, Park J, Tran H, Hu L S, Hemmings B A, Greenberg M E. Protein kinase SGK mediates survival signals by phosphorylating the forkhead transcription factor FKHRL1 (FOXO3a). Mol Cell Biol 2001; 21:952-65
5: Mikosz C A, Brickley D R, Sharkey M S, Moran T W, Conzen S D. Glucocorticoid receptor-mediated protection from apoptosis is associated with induction of the serine/threonine survival kinase gene, sgk-1. J Biol. Chem. 2001; 276:16649-54.
6: Zuo Z, Urban G, Scammell J G, Dean N M, McLean T K, Aragon I, Honkanen R E. Ser/Thr protein phosphatase type 5 (PP5) is a negative regulator of glucocorticoid receptor-mediated growth arrest. Biochemistry. 1999; 38:8849-57.
7: Buse P, Tran S H, Luther E, Phu P T, Aponte G W, Firestone G L. Cell cycle and hormonal control of nuclear-cytoplasmic localisation of the serum- and glucocorticoid-inducible protein kinase, Sgk, in mammary tumour cells. A novel convergence point of anti-proliferative and proliferative cell signalling pathways. J Biol. Chem. 1999; 274:7253-63.

SUMMARY OF THE INVENTION

The invention relates to compounds of the formula I

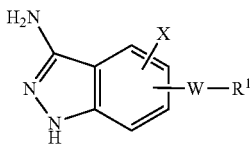

in which
W denotes $-[C(R^2)_2]_n-$, $-[C(R^2)_2]_nCONR^2[C(R^2)_2]_n-$, $-[C(R^2)_2]_nCONR^2NR^2[C(R^2)_2]_n-$, $-[C(R^2)_2]_nNR^2CO[C(R^2)_2]_n-$, $-[C(R^2)_2]_nNR^2CO[C(R^2)_2]_nNR^2-$, $-[C(R^2)_2]_nO[C(R^2)_2]_n-[C(R^2)_2]_nNR^2[C(R^2)_2]_n-$, $-[C(R^2)_2]_nN[C(R^2)_2R^1][C(R^2)_2]_n-$, $-[C(R^2)_2]_nO[C(R^2)_2]_nCONR^2[C(R^2)_2]_n-$, $-[C(R^2)_2]_nNR^2[C(R^2)_2]_nCONR^2[C(R^2)_2]_n-$, $-[C(R^2)_2]_nNR^2COO[C(R^2)_2]_n-$, $-[C(R^2)_2]_nCO[C(R^2)_2]_n-$, $-[C(R^2)_2]_nCOO[C(R^2)_2]_n-$, $-C(R^2)=C(R^2)CONR^2[C(R^2)_2]_n$ or $-C(R^2)=N-NR^2CO[C(R^2)_2]_n$,
X denotes H, Hal, A, $OR^2$, $N(R^2)_2$, $NO_2$, CN, $COOR^2$, $CON(R^2)_2$, $NR^2COA$, $NR^2SO_2A$, $COR^2$ or $SO_2NR^2$,
$R^1$ denotes a mono- or bicyclic saturated or unsaturated carbo- or heterocycle having 0 to 4 N, O and/or S atoms, which may be mono-, di- or trisubstituted by $R^2$, Hal, A, $-[C(R^3)_2]_n-Ar$, $-[C(R^3)_2]_n-Het$, $-O-[C(R^2)_2]_n-Het$, $-[C(R^3)_2]_n-cycloalkyl$, $OR^2$, $N(R^2)_2$, $NO_2$, CN, $-[C(R^2)_2]_nCOOR^2$, $O-[C(R^2)_2]_nCOOR^2$, $-[C(R^2)_2]_nCON(R^2)_2$, $-[C(R^2)_2]_nCONR^2N(R^2)_2$, $O-[C(R^2)_2]_oCON(R^2)_2$, $O-[C(R^2)_2]_oCONR^2N(R^2)_2$, $NR^2COA$, $NR^2CON(R^2)_2$, $NR^2SO_2A$, $COR^2$, $SO_2NR^2$, $S(O)_mA$, $=S$, $=NR^3$ and/or $=O$ (carbonyl oxygen),
$R^2$ denotes H, A, $-[C(R^3)_2]_n-Ar'$, $-[C(R^3)_2]_n-Het'$, $-[C(R^3)_2]_n-cycloalkyl$, $-[C(R^3)_2]_n-OR^3$, $-[C(R^3)_2]_n-COOA$ or $-[C(R^3)_2]_nN(R^3)_2$,
$R^3$ denotes H or A,
A denotes unbranched or branched alkyl having 1-10 C atoms, in which one or two $CH_2$ groups may be replaced by O or S atoms and/or by $-CH=CH-$ groups and/or, in addition, 1-7H atoms may be replaced by F,
Ar denotes phenyl, naphthyl or biphenyl, each of which is unsubstituted or mono-, di- or trisubstituted by Hal, A, $OR^2$, $N(R^2)_2$, $NO_2$, CN, $COOR^2$, $CON(R^2)_2$, $NR^2COA$, $NR^2CON(R^2)_2$, $NR^2SO_2A$, $COR^2$, $SO_2N(R^2)_2$, $S(O)_mA$, $-[C(R^3)_2]_n-COOR^2$ or $-O[C(R^3)_2]_o-COOR^2$,
Ar' denotes phenyl, naphthyl or biphenyl, each of which is unsubstituted or mono-, di- or trisubstituted by Hal, A, $OR^3$, $N(R^3)_2$, $NO_2$, CN, $COOR^3$, $CON(R^3)_2$, $NR^3COA$, $NR^3CON(R^3)_2$, $NR^3SO_2A$, $COR^3$, $SO_2N(R^3)_2$, $S(O)_mA$, $-[C(R^3)_2]_n-COOR^3$ or $-O[C(R^3)_2]_o-COOR^3$,
Het denotes a mono- or bicyclic saturated or unsaturated heterocycle having 1 to 4 N, O and/or S atoms, which may be mono-, di- or trisubstituted by $R^2$, Hal, A, $-[C(R^3_2)]_n-Ar$, $-[C(R^3)_2]_n-Het$, $-[C(R^3)_2]_n-cycloalkyl$, $OR^2$, $N(R^2)_2$, $NO_2$, CN, $-[C(R^2)_2]_nCOOR^2$, $O-[C(R^2)_2]_nCOOR^2$, $-[C(R^2)_2]_nCON(R^2)_2$, $-[C(R^2)_2]_nCONR^2N(R^2)_2$, $O-[C(R^2)_2]_oCON(R^2)_2$, $O-[C(R^2)_2]_oCONR^2N(R^2)_2$, $NR^2COA$, $NR^2CON(R^2)_2$, $NR^2SO_2A$, $COR^2$, $SO_2NR^2$, $S(O)_mA$ and/or $=O$ (carbonyl oxygen),
Het' denotes a mono- or bicyclic saturated or unsaturated heterocycle having 1 to 4 N, O and/or S atoms, which may be mono-, di- or trisubstituted by $R^3$, Hal, A, $OR^2$, $N(R^3)_2$, $NO_2$, CN, $COOR^3$, $CON(R^3)_2$, $NR^3COA$, $NR^3SO_2A$, $COR^3$, $SO_2NR^3$, $S(O)_mA$, $=S$, $=NR^3$ and/or $=O$ (carbonyl oxygen),
Hal denotes F, Cl, Br or I,
m denotes 0, 1 or 2,
n denotes 0, 1, 2, 3 or 4,
o denotes 1, 2 or 3, and pharmaceutically usable derivatives, salts, solvates and stereoisomers thereof, including mixtures thereof in all ratios.

The invention relates to the compounds of the formula I and salts thereof and to a process for the preparation of compounds of the formula I according to Claims 1-16 and pharmaceutically usable derivatives, solvates, salts and stereoisomers thereof, characterised in that a) for the preparation of compounds of the formula I in which
W denotes i) $-[C(R^3)_2]_nCONH[C(R^3)_2]_n-$ or
ii) $-[C(R^3)_2]_nCONHNH[C(R^3)_2]_n-$, a compound of the formula II

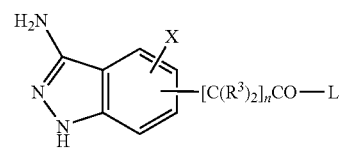

in which
X, $R^3$ and n have the meaning indicated in Claim 1,
and L denotes Cl, Br, I or a free or reactively functionally modified OH group, is reacted with i) a compound of the formula IIIa $$H_2N[C(R^3)_2]_n\text{—}R^1 \qquad \text{IIIa}$$

in which
$R^1$, $R^3$ and n have the meanings indicated in Claim 1, or ii) a compound of the formula IIIb $$H_2N\text{—}NH[C(R^3)_2]_n\text{—}R^1 \qquad \text{IIIb}$$

in which
$R^1$, $R^3$ and n have the meanings indicated in Claim 1, or b) for the preparation of compounds of the formula I in which W denotes $-[C(R^3)_2]_n NHCO[C(R^3)_2]_n-$, a compound of the formula IV in which X, $R^3$ and n have the meanings indicated in Claim 1, is reacted with a compound of the formula V $$L\text{-}CO\text{—}[C(R^3)_2]_n\text{—}R^1 \qquad V$$

in which
L denotes Cl, Br, I or a free or reactively functionally modified OH group and
$R^1$, $R^3$ and n have the meanings indicated in Claim 1, or c) for the preparation of compounds of the formula I in which W denotes $-[C(R^3)_2]_n-$, $-[C(R^3)_2]_n O[C(R^3)_2]_n-$, $-[C(R^3)_2]_n CO[C(R^3)_2]_n-$ $-[C(R^3)_2]_n NR^3 [C(R^3)_2]_n-$ or $-[C(R^3)_2]_n NR^1 [C(R^3)_2]_n-$, a compound of the formula VI in which
$R^1$, W and X have the meanings indicated in Claim 1, is reacted with hydrazine, or d) for the preparation of compounds of the formula I in which W denotes $-[C(R^3)_2]_n NHCONH[C(R^3)_2]_n-$, a compound of the formula IV is reacted with a compound of the formula VII $$O\text{=}C\text{=}N\text{—}[C(R^3)_2]_n\text{—}R^1 \qquad \text{VII}$$

in which $R^1$, $R^3$ and n have the meanings indicated in Claim 1, or e) in that they are liberated from one of their functional derivatives by treatment with a solvolysing or hydrogenolysing agent, and/or a base or acid of the formula I is converted into one of its salts.

The invention also relates to the stereoisomers (E, Z isomers) and the hydrates and solvates of these compounds. Solvates of the compounds are taken to mean adductions of inert solvent molecules onto the compounds which form owing to their mutual attractive force. Solvates are, for example, mono- or dihydrates or alcoholates.

Pharmaceutically usable derivatives is taken to mean, for example, the salts of the compounds according to the invention and also so-called prodrug compounds.

Prodrug derivatives is taken to mean compounds of the formula I which have been modified, with, for example, alkyl or acyl groups, sugars or oligopeptides and which are rapidly cleaved in the organism to form the active compounds according to the invention.

These also include biodegradable polymer derivatives of the compounds according to the invention, as is described, for example, in Int. J. Pharm. 115, 61-67 (1995).

The expression "effective amount" means the amount of a medicament or pharmaceutical active ingredient which causes a biological or medical response which is sought or aimed at, for example by a researcher or physician, in a tissue, system, animal or human.

In addition, the expression "therapeutically effective amount" means an amount which, compared with a corresponding subject who has not received this amount, has the following consequence:

improved treatment, healing, prevention or elimination of a disease, syndrome, condition, complaint, disorder or prevention of side effects or also the reduction in the progress of a disease, condition, disorder or side effects or also the reduction in the progress of a disease, condition or disorder.

The expression "therapeutically effective amount" also encompasses the amounts which are effective for increasing normal physiological function.

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

For all radicals which occur more than once, such as, for example, $R^2$, $R^3$ or n, their meanings are independent of one another.

Above and below, the radicals and parameters W, X and $R^1$ have the meanings indicated for the formula I, unless expressly indicated otherwise.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Cycloalkyl preferably denotes cyclopropyl, cyclobutyl, cyclopentyl, cyclohexyl or cycloheptyl.

W preferably denotes $-[C(R^2)_2]_n-$, $-[C(R^2)_2]_nCONR^2[C(R^2)_2]_n-$, $-[C(R^2)_2]_nNR^2CO[C(R^2)_2]_nNR^2-$, $-[C(R^2)_2]_nO[C(R^2)_2]_n-$, $-[C(R^2)_2]_nNR^2[C(R^2)_2]_n-$, $-[C(R^2)_2]_nN[C(R^2)_2R^1][C(R^2)_2]_n-$, $-[C(R^2)_2]_nCO[C(R^2)_2]_n-$, $-[C(R^2)_2]_nNR^2[C(R^2)_2]_nCONR^2[C(R^2)_2]_n-$, $-[C(R^2)_2]_nCONR^2NR^2[C(R^2)_2]_n-$ or $-[C(R^2)_2]_nNR^2CO[C(R^2)_2]_n-$; particularly preferably $-[C(R^3)_2]_n-$, $-[C(R^3)_2]_nCONH[C(R^3)_2]_n-$, $-[C(R^3)_2]_nNR^3CO[C(R^3)_2]_nNR^3-$, $-[C(R^3)_2]_nO[C(R^3)_2]_n-$, $-[C(R^3)_2]_nNR^3[C(R^3)_2]_n-$, $-[C(R^3)_2]_nCO[C(R^3)_2]_n-$, $-[C(R^3)_2]_nN[C(R^3)_2R^1][C(R^3)_2]_n-$, $-[C(R^3)_2]_nNR^3C(R^3)_2]_nCONR^3[C(R^3)_2]_n-$, $-[C(R^3)_2]_nCONHNH[C(R^3)_2]_n-$, $-[C(R^3)_2]_nNHCO[C(R^3)_2]_n-$, $-C(R^3)=C(R^3)CONR^3[C(R^3)_2]_n$ or $-C(R^3)=N-NR^3CO[C(R^3)_2]_n$.

W particularly preferably denotes $(CH_2)_n$, $CONH(CH_2)_n$, $NHCO(CH_2)_n$, $CONHNH$, $O$, $O(CH_2)_n$, $NHCO$, $CONH$, $CO$, $NH(CH_2)_n$, $N[(CH_2)_nR^1](CH_2)_n$, $NHCO-(CH_2)_nNH$, $NHCONH$, $CONHCHR^3$, $-CH=CH-CONH(CH_2)_n$ or $-CH=N-NHCO(CH_2)_n$.

W very particularly preferably denotes a bond, CONHCH$_2$, NHCOCH$_2$, CONHNH, O, OCH$_2$, NHCO, CONH, CONH(CH$_2$)$_2$, CO, NHCH$_2$, N(CH$_2$R$^1$)CH$_2$, NHCO—CH$_2$NH, NHCONH, NHCO(CH$_2$)$_2$, CONHCHR$^3$, $-CH=CH-CONH(CH_2)_n$ or $-CH=N-NHCO(CH_2)_n$.

X preferably denotes H.

$R^1$ preferably denotes a mono- or bicyclic saturated or unsaturated carbo- or heterocycle having 0 to 4 N, O and/or S atoms, which may be mono-, di- or trisubstituted by Hal, A, $-(CH_2)_nOH$, OA, phenyl, phenoxy, benzyloxy, pyridin-4-ylmethyl-, piperidin-4-oxy-, NO$_2$, CN, $-(CH_2)_nCOOR^3$, $O-(CH_2)_nCOOR^3$, SO$_2$A, NHCOA, $(CH_2)_nNH_2$, $(CH_2)_nNHA$, $(CH_2)_nNA_2$, $-[C(R^2)_2]_nCONH_2$, $(CH_2)_nCONHNH_2$ or $O-(CH_2)_nCONHNH_2$.

Saturated carbocycle preferably denotes cyclopentyl or cyclohexyl. Unsaturated carbocycle preferably denotes phenyl, naphthyl or biphenyl, particularly preferably phenyl.

In a further embodiment, $R^1$ preferably denotes a mono- or bicyclic unsaturated carbocycle, which may be mono-, di- or trisubstituted by Hal, A, $-(CH_2)_nOH$, OA, phenyl, phenoxy, benzyloxy, pyridin-4-ylmethyl-, piperidin-4-oxy-, NO$_2$, CN, $-(CH_2)_nCOOR^3$, $O-(CH_2)_nCOOR^3$, SO$_2$A, NHCOA, $(CH_2)_nNH_2$, $(CH_2)_nNHA$, $(CH_2)_nNA_2$, $-[C(R^2)_2]_nCONH_2$, $(CH_2)_nCONHNH_2$ or $O-(CH_2)_nCONHNH_2$.

In a further embodiment, $R^1$ particularly preferably denotes phenyl or naphthyl, each of which may be mono-, di- or trisubstituted by Hal, A, $-(CH_2)_nOH$, OA, phenyl, phenoxy, benzyloxy, pyridin-4-ylmethyl-, piperidin-4-oxy-, NO$_2$, CN, $-(CH_2)_nCOOR^{13}$, $O-(CH_2)_nCOOR^3$, SO$_2$A, NHCOA, $(CH_2)_nNH_2$, $(CH_2)_nNHA$, $(CH_2)_nNA_2$, $-[C(R^2)_2]_nCONH_2$, $(CH_2)_nCONHNH_2$ or $O-(CH_2)_nCONHNH_2$.

In another embodiment, $R^1$ preferably denotes a mono- or bicyclic saturated or unsaturated heterocycle having 1 to 4 N, O and/or S atoms which is unsubstituted or mono- or disubstituted by NH$_2$, A, OH, CH$_2$OH, COOH and/or COOA.

Unsubstituted mono- or bicyclic saturated or unsaturated heterocycle having 1 to 4 N, O and/or S atoms preferably denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, 4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

$R^1$ particularly preferably also denotes 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, 1,3-benzodioxol-5-yl, 1,4-benzodioxan-6-yl, 2,1,3-benzothiadiazol-4- or -5-yl or 2,1,3-benzoxadiazol-5-yl, 2-, 3- or 4-piperidinyl, 2-, 3- or 4-morpholinyl, 1-, 2- or 3-piperazinyl, 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl, 3,4-dihydro-2H-1,5-benzodioxepin-6- or -7-yl, 2,3-dihydrobenzofuranyl or 2,3-dihydro-2-oxofuranyl, each of which is unsubstituted or mono- or disubstituted by NH$_2$, A, OH, CH$_2$OH, COOH and/or COOA.

$R^1$ furthermore preferably denotes phenyl or naphthyl, each of which may be mono-, di- or trisubstituted by Hal, A, $-(CH_2)_nOH$, OA, phenyl, phenoxy, benzyloxy, pyridin-4-ylmethyl-, piperidin-4-oxy-, NO$_2$, CN, $-(CH_2)_nCOOR^3$, O—$(CH_2)_n COOR^3$, $SO_2A$, NHCOA, $(CH_2)_n NH_2$, $(CH_2)_n NHA$, $(CH_2)_n NA_2$, —$[C(R^2)_2]_n CONH_2$, $(CH_2)_n CONHNH_2$ or O—$(CH_2)_n CONHNH_2$, or a mono- or bicyclic saturated or unsaturated heterocycle having 1 to 4 N, O and/or S atoms which is unsubstituted or mono- or disubstituted by $NH_2$, A, OH, $CH_2OH$, COOH and/or COOA.

$R^2$ preferably denotes H or A, furthermore also phenyl, benzyl or $[C(R^3)_2]_n COOA$, such as, for example, $CH_2COOCH_3$.

—COA (acyl) preferably denotes acetyl, propionyl, furthermore also butyryl, pentanoyl, hexanoyl or, for example, benzoyl.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino) phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-phenoxyphenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar preferably denotes, for example, phenyl which is unsubstituted or mono-, di- or trisubstituted by Hal, A, $OR^2$, $OR^3$, $SO_2A$, $COOR^2$ or CN.

Ar particularly preferably denotes, for example, phenyl which is unsubstituted or mono- or disubstituted by Hal, A, OA, phenoxy, $SO_2A$, $SO_2NH_2$, $COOR^2$ or CN, such as, for example, phenyl, 2-methylsulfonylphenyl, 2-aminosulfonylphenyl, phenoxyphenyl, 2-, 3- or 4-chlorophenyl, 3,4-dichlorophenyl, 4-methylphenyl, 4-bromophenyl, 3-fluoro-4-methoxyphenyl, 4-trifluoromethoxyphenyl, 4-ethoxyphenyl, 2-methoxyphenyl, 3-cyanophenyl, 4-ethoxycarbonylphenyl, methoxycarbonylphenyl, carboxyphenyl or aminocarbonylphenyl.

Ar' preferably denotes, for example, phenyl which is unsubstituted or mono-, di- or trisubstituted by Hal, A, $OR^2$, $OR^3$, $SO_2A$, $COOR^2$ or CN.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-innolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated.

Het may thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Het' preferably denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated.

Het' may thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or 4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1H-isoquinolin-2-yl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ik, which conform to the formula I and in which the radicals not designated in greater detail have the meaning indicated for the formula I, but in which in Ia W denotes $-[C(R^3)_2]_n-$, $-[C(R^3)_2]_n CONH[C(R^3)_2]_n-$, $-[C(R^3)_2]_n NR^3 CO[C(R^3)_2]_n NR^3-$, $-[C(R^3)_2]_n O[C(R^3)_2]_n-$, $-[C(R^3)_2]_n NR^3[C(R^3)_2]_n-$, $-[C(R^3)_2]_n N[C(R^3)_2 R^1][C(R^3)_2]_n-$, $-[C(R^3)_2]_n NR^3 C(R^3)_2]_n CONR^3[C(R^3)_2]_n-$, $-[C(R^3)_2]_n CO[C(R^3)_2]_n-$, $-[C(R^3)_2]_n CONHNH[C(R^3)_2]_n-$, $-[C(R^3)_2]_n NHCO[C(R^3)_2]_n-$, $-C(R^3)=C(R^3)CONR^3[C(R^3)_2]_n$ or $-C(R^3)=N-NR^3 CO[C(R^3)_2]_n$;

in Ib W denotes $(CH_2)_n$, $CONH(CH_2)_n$, $NHCO(CH_2)_n$, $CONHNH$, $O$, $O(CH_2)_n$, $NHCO$, $CONH$, $CO$, $NH(CH_2)_n$, $N[(CH_2)_n R^1](CH_2)_n$, $NHCO-(CH_2)_n NH$, $NHCONH$, $CONHCHR^3$, $-CH=CH-CONH([CH_2)_n$ or $-CH=N-NHCOCH_2)_n$;

in Ic X denotes H;

in Id $R^1$ denotes a mono- or bicyclic saturated or unsaturated carbo- or heterocycle having 0 to 4 N, O and/or S atoms, which may be mono-, di- or trisubstituted by Hal, A, $-(CH_2)_n OH$, OA, phenyl, phenoxy, benzyloxy, pyridin-4-ylmethyl-, piperidin-4-oxy-, $NO_2$, CN, $-(CH_2)_n COOR^3$, $O-(CH_2)_n COOR^3$, $SO_2 A$, NHCOA, $(CH_2)_n NH_2$, $(CH_2)_n NHA$, $(CH_2)_n NA_2$, $-[C(R^2)_2]_n CONH_2$, $(CH_2)_n CONHNH_2$ or $O-(CH_2)_n CONHNH_2$;

in Ie $R^1$ denotes a mono- or bicyclic unsaturated carbocycle, which may be mono-, di- or trisubstituted by Hal, A, $-(CH_2)_n OH$, OA, phenyl, phenoxy, benzyloxy, pyridin-4-ylmethyl-, piperidin-4-oxy-, $NO_2$, CN, $-(CH_2)_n COOR^3$, $O-(CH_2)_n COOR^3$, $SO_2 A$, NHCOA, $(CH_2)_n NH_2$, $(CH_2)_n NHA$, $(CH_2)_n NA_2$, $-[C(R^2)_2]_n CONH_2$, $(CH_2)_n CONHNH_2$ or $O-(CH_2)_n CONHNH_2$;

in If $R^1$ denotes phenyl or naphthyl, each of which may be mono-, di- or trisubstituted by Hal, A, $-(CH_2)_n OH$, OA, phenyl, phenoxy, benzyloxy, pyridin-4-ylmethyl-, piperidin-4-oxy-, $NO_2$, CN, $-(CH_2)_n COOR^3$, $O-(CH_2)_n COOR^3$, $SO_2 A$, NHCOA, $(CH_2)_n NH_2$, $(CH_2)_n NHA$, $(CH_2)_n NA_2$, $-[C(R^2)_2]_n CONH_2$, $(CH_2)_n CONHNH_2$ or $O-(CH_2)_n CONHNH_2$;

in Ig $R^1$ denotes a mono- or bicyclic saturated or unsaturated heterocycle having 1 to 4 N, O and/or S atoms, which is unsubstituted or mono- or disubstituted by $NH_2$, A, OH, $CH_2 OH$, COOH and/or COOA;

in Ih $R^1$ denotes 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, 1,3-benzodioxol-5-yl, 1,4-benzodioxan-6-yl, 2,1,3-benzothiadiazol-4- or -5-yl or 2,1,3-benzoxadiazol-5-yl, 2-, 3- or 4-piperidinyl, 2-, 3- or 4-morpholinyl, 1-, 2- or 3-piperazinyl, 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy) phenyl, 3,4-dihydro-2H-1,5-benzodioxepin-6- or -7-yl, 2,3-dihydrobenzofuranyl, 2,3-dihydro-2-oxofuranyl or 3,4-dihydro-1H-isoquinolin-2-yl, each of which is unsubstituted or mono- or disubstituted by $NH_2$, A, OH, $CH_2 OH$, COOH and/or COOA;

in Ii A denotes unbranched or branched alkyl having 1-6 C atoms, in which 1-7H atoms may be replaced by F;

in Ij W denotes $-[C(R^3)_2]_n-$, $-[C(R^3)_2]_n CONH[C(R^3)_2]_n-$, $-[C(R^3)_2]_n NR^3 CO[C(R^3)_2]_n NR^3-$, $-[C(R^3)_2]_n O[C(R^3)_2]_n-$, $-[C(R^3)_2]_n NR^3[C(R^3)_2]_n-$, $-[C(R^3)_2]_n N[C(R^3)_2 R^1][C(R^3)_2]_n-$, $-[C(R^3)_2]_n NR^3 C(R^3)_2]_n CONR^3[C(R^3)_2]_n-$, $-[C(R^3)_2]_n CO[C(R^3)_2]_n-$, $-[C(R^3)_2]_n CONHNH[C(R^3)_2]_n-$, $-[C(R^3)_2]_n NHCO[C(R^3)_2]_n-$, $-C(R^3)=C(R^3)CONR^3[C(R^3)_2]_n$ or $-C(R^3)=N-NR^3 CO[C(R^3)_2]_n$, X denotes H, $R^1$ denotes a mono- or bicyclic saturated or unsaturated carbo- or heterocycle having 0 to 4 N, O and/or S atoms, which may be mono-, di- or trisubstituted by Hal, A, $-(CH_2)_n OH$, OA, phenyl, phenoxy, benzyloxy, pyridin-4-ylmethyl-, piperidin-4-oxy-, $NO_2$, CN, $-(CH_2)_n COOR^3$, $O-(CH_2)_n COOR^3$, $SO_2 A$, NHCOA, $(CH_2)_n NH_2$, $(CH_2)_n NHA$, $(CH_2)_n NA_2$, $-[C(R^2)_2]_n CONH_2$, $(CH_2)_n CONHNH_2$ or $O-(CH_2)_n CONHNH_2$, $R^3$ denotes H or A, A denotes unbranched or branched alkyl having 1-6 C atoms, in which 1-7H atoms may be replaced by F, Hal denotes F, Cl, Br or I, n denotes 0, 1 or 2;

in Ik W denotes $-[C(R^3)_2]_n-$, $-[C(R^3)_2]_n CONH[C(R^3)_2]_n-$, $-[C(R^3)_2]_n NR^3 CO[C(R^3)_2]_n NR^3-$, $-[C(R^3)_2]_n O[C(R^3)_2]_n-$, $-[C(R^3)_2]_n NR^3[C(R^3)_2]_n-$, $-[C(R^3)_2]_n N[C(R^3)_2 R^1][C(R^3)_2]_n-$, $-[C(R^3)_2]_n NR^3 C(R^3)_2]_n CONR^3[C(R^3)_2]_n-$, $-[C(R^3)_2]_n CO[C(R^3)_2]_n-$, $-[C(R^3)_2]_n CONHNH[C(R^3)_2]_n-$, $-[C(R^3)_2]_n NHCO[C(R^3)_2]_n-$, $-C(R^3)=C(R^3)CONR^3[C(R^3)_2]_n$ or $-C(R^3)=N-NR^3 CO[C(R^3)_2]_n$, X denotes H, $R^1$ denotes phenyl or naphthyl, each of which may be mono-, di- or trisubstituted by Hal, A, $-(CH_2)_n OH$, OA, phenyl, phenoxy, benzyloxy, pyridin-4-ylmethyl-, piperidin-4-oxy-, $NO_2$, CN, $-(CH_2)_n COOR^3$, $O-(CH_2)_n COOR^3$, $SO_2 A$, NHCOA, $(CH_2)_n NH_2$, $(CH_2)_n NHA$, $(CH_2)_n NA_2$, $-[C(R^2)_2]_n CONH_2$, $(CH_2)_n CONHNH_2$ or $O-(CH_2)_n CONHNH_2$, or a mono- or bicyclic saturated or unsaturated heterocycle having 1 to 4 N, O and/or S atoms, which is unsubstituted or mono- or disubstituted by $NH_2$, A, OH, $CH_2OH$, COOH and/or COOA, $R^3$ denotes H or A, A denotes unbranched or branched alkyl having 1-6 C atoms, in which 1-7H atoms may be replaced by F, Hal denotes F, Cl, Br or I, n denotes 0, 1 or 2;

and pharmaceutically usable derivatives, solvates, salts and stereoisomers thereof, including mixtures thereof in all ratios.

The compounds according to the invention and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se, which are not mentioned here in greater detail.

If desired, the starting materials can also be formed in situ so that they are not isolated from the reaction mixture, but instead are immediately converted further into the compounds according to the invention.

The starting compounds are generally known. If they are novel, however, they can be prepared by methods known per se.

Compounds of the formula I in which

W denotes i) —$[C(R^3)_2]_n$CONH$[C(R^3)_2]_n$— or
ii) —$[C(R^3)_2]_n$CONHNH$[C(R^3)_2]_n$— can preferably be obtained by reacting compounds of the formula II with compounds of the formula IIIa or IIIb.

The reaction is generally carried out in an inert solvent, in the presence of an acid-binding agent, preferably an organic base, such as DIPEA, triethylamine, dimethylaniline, pyridine or quinoline, or an excess of the carboxyl component of the formula II.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

It may also be favourable to add an alkali or alkaline earth metal hydroxide, carbonate or bicarbonate or another salt of a weak acid of the alkali or alkaline earth metals, preferably of potassium, sodium, calcium or caesium. Depending on the conditions used, the reaction time is between a few minutes and 14 days, the reaction temperature is between about −30° and 140°, normally between −10° and 90°, in particular between about 0° and about 70°.

In the compounds of the formula II, L preferably denotes Cl, Br, I or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy). Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example by addition of HOBt or N-hydroxysuccinimide.

Compounds of the formula I in which W denotes —$[C(R^3)_2]_n$NHCO$[C(R^3)_2]_n$— can further preferably be obtained by reacting compounds of the formula IV with compounds of the formula V.

The reaction is generally carried out in an inert solvent and under conditions as indicated above.

In the compounds of the formula V, L preferably denotes Cl, Br, I or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

Compounds of the formula I in which

W denotes —$[C(R^3)_2]_n$—, —$[C(R^3)_2]_n$O$[C(R^3)_2]_n$—, —$[C(R^3)_2]_n$NR$^3$$[C(R^3)_2]_n$— or —$[C(R^3)_2]_n$NR$^1$$[C(R^3)_2]_n$— can further preferably be obtained by reacting compounds of the formula VI with hydrazine.

The reaction is generally carried out in an inert solvent and under conditions as indicated above.

Compounds of the formula I in which

W denotes —$[C(R^3)_2]_n$NHCONH$[C(R^3)_2]_n$— can further preferably be obtained by reacting compounds of the formula IV with compounds of the formula VII.

The reaction is generally carried out in an inert solvent and under conditions as indicated above.

Compounds of the formula I can furthermore be obtained by liberating compounds of the formula I from one of their functional derivatives by treatment with a solvolysing or hydrogenolysing agent.

Preferred starting materials for the solvolysis or hydrogenolysis are those which otherwise conform to the formula I, but contain corresponding protected amino and/or hydroxyl groups instead of one or more free amino and/or hydroxyl groups, preferably those which carry an amino-protecting group instead of an H atom bonded to an N atom, in particular those which carry an R'—N group, in which R' denotes an amino-protecting group, instead of an HN group and/or those which carry a hydroxyl-protecting group instead of the H atom of a hydroxyl group, for example those which conform to the formula I, but carry a —COOR" group, in which R" denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, p-nitrobenzoyl, 4-methoxybenzyl, p-toluenesulfonyl, tert-butyl and acetyl, where benzyl and tert-butyl are particularly preferred.

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut and Mtr groups can, for example, preferably be cleaved off using TFA in dichloromethane or using approximately 3 to 5N HCl in dioxane at 15-300, and the FMOC group can be cleaved off using an approximately 5 to 50% solution of dimethylamine, diethylamine or piperidine in DMF at 15-30°.

Hydrogenolytically removable protecting groups (for example CBZ, benzyl or the liberation of the amidino group from its oxadiazole derivative) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be saponified, for example, using acetic acid or using NaOH or KOH in water, water/THF or water/dioxane at temperatures between 0 and 100°.

Furthermore, free amino groups can be acylated in a conventional manner using an acid chloride or anhydride or alkylated using an unsubstituted or substituted alkyl halide, or reacted with $CH_3-C(=NH)-OEt$, advantageously in an inert solvent, such as dichloromethane or THF, and/or in the presence of a base, such as triethylamine or pyridine, at temperatures between −60 and +30°.

The invention also relates to the intermediate compounds selected from the group

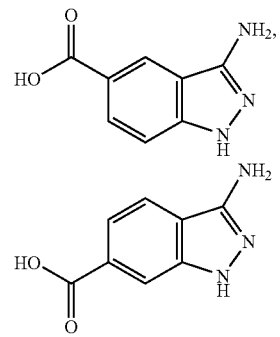

and salts thereof.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Compounds of the formula I according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds and/or physiologically acceptable salts thereof for the preparation of a medicament (pharmaceutical composition), in particular by non-chemical methods. They can be converted into a suitable dosage form here together with at least one solid, liquid and/or semi-liquid excipient or adjuvant and, if desired, in combination with one or more further active ingredients.

The invention furthermore relates to medicaments comprising at least one compound according to the invention and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the present invention depends on a number of factors, including, for example, the age and weight of the human or animal, the precise disease condition which requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound according to the invention and/or pharmaceutically usable derivatives, solvates and stereoisomers thereof, including mixtures thereof in all ratios, and at least one further medicament active ingredient.

The invention also relates to a set (kit) consisting of separate packs of
(a) an effective amount of a compound according to the invention and/or pharmaceutically usable derivatives, solvates and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Use

The present compounds are suitable as pharmaceutical active ingredients for mammals, in particular for humans, in the treatment of SGK-induced diseases.

The invention thus relates to the use of compounds according to Claim 1 and to pharmaceutically usable derivatives, solvates and stereoisomers, including mixtures thereof in all ratios, for the preparation of a medicament for the treatment of diseases in which the inhibition, regulation and/or modulation of kinase signal transduction plays a role.

Preference is given here to SGK.

Preference is given to the use of compounds according to claim 1 and pharmaceutically usable derivatives, solvates and stereoisomers thereof, including mixtures thereof in all ratios, for the preparation of a medicament for the treatment of diseases which are influenced by inhibition of SGKs by the compounds according to Claim 1.

The present invention encompasses the use of the compounds according to Claim 1 according to the invention and/or physiologically acceptable salts and solvates thereof for the preparation of a medicament for the treatment or prevention of diabetes (for example diabetes mellitus, diabetic nephropathy, diabetic neuropathy, diabetic angiopathy and microangiopathy), obesity, metabolic syndrome (dyslipidaemia), systemic and pulmonary hypertonia, cardiovascular diseases (for example cardial fibroses after myocardial infarction, cardiac hypertrophy and cardiac insufficiency, arteriosclerosis) and renal diseases (for example glomerulosclerosis, nephrosclerosis, nephritis, nephropathy, electrolyte excretion disorder), generally in fibrosis and inflammatory processes of any type (for example liver cirrhosis, pulmonary fibrosis, fibrosing pancreatitis, rheumatism and arthritis, Crohn's disease, chronic bronchitis, radiation fibrosis, sclerormatitis, cystic fibrosis, scarring, Alzheimer's disease). The compounds according to the invention can also inhibit the growth of cancer, tumour cells and tumour metastases and are therefore suitable for tumour therapy.

The compounds according to the invention are furthermore used for the treatment of coagulopathies, such as, for example, dysfibrinogenaemia, hypoproconvertinaemia, haemophilia B, Stuart-Prower defect, prothrombin complex deficiency, consumption coagulopathy, hyperfibrinolysis, immunocoagulopathy or complex coagulopathies, and also in neuronal excitability, for example epilepsy. The compounds according to the invention can also be employed therapeutically in the treatment of a glaucoma or cataract. The compounds according to the invention are furthermore used in the treatment of bacterial infections and in antiinfection therapy. The compounds according to the invention can also be employed therapeutically for increasing learning ability and attention.

Preference is given to the use of compounds according to Claim 1 and pharmaceutically usable derivatives, solvates and stereoisomers thereof, including mixtures thereof in all ratios, for the preparation of a medicament for the treatment or prevention of diabetes, obesity, metabolic syndrome (dyslipidaemia), systemic and pulmonary hypertonia, cardiovascular diseases and renal diseases, generally in fibrosis and inflammatory processes of any type, cancer, tumour cells, tumour metastases, coagulopathies, neuronal excitability, glaucoma, cataract, bacterial infections and in antiinfection therapy, for increasing learning ability and attention.

Diabetes is preferably diabetes mellitus, diabetic nephropathy, diabetic neuropathy, diabetic angiopathy and microangiopathy.

Cardiovascular diseases are preferably cardial fibroses after myocardial infarction, cardiac hypertrophy, cardiac insufficiency and arteriosclerosis.

Renal diseases are preferably glomerulosclerosis, nephrosclerosis, nephritis, nephropathy and electrolyte excretion disorders.

Fibroses and inflammatory processes are preferably liver cirrhosis, pulmonary fibrosis, fibrosing pancreatitis, rheumatism and arthritis, Crohn's disease, chronic bronchitis, radiation fibrosis, sclerormatitis, cystic fibrosis, scarring, Alzheimer's disease.

Assays

The compounds according to the invention described in the examples were tested in the assays described below and were found to have kinase-inhibitory activity. Further assays are known from the literature and could easily be performed by the person skilled in the art (see, for example, Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., *In Vitro* 18:538-549).

Above and below, all temperatures are indicated in ° C. In the following examples, "conventional work-up" means: if necessary, water is added, the pH is adjusted, if necessary, to between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS): EI (electron impact ionisation) M⁺

FAB (fast atom bombardment) (M+H)⁺

ESI (electrospray ionisation) (M+H)⁺ (unless indicated otherwise)

EXAMPLE 1

The preparation of N-3-chlorobenzyl-3-amino-1H-indazole-5-carboxamide ("1") is carried out analogously to the following scheme:

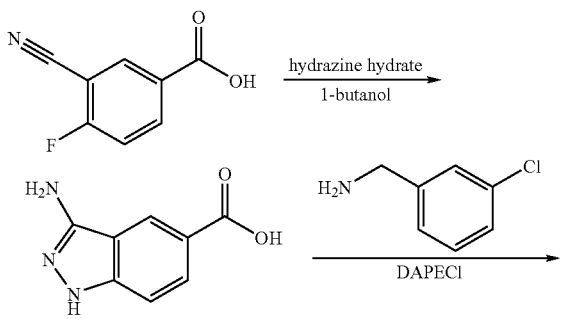

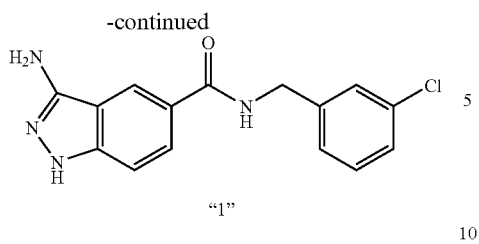

"1"

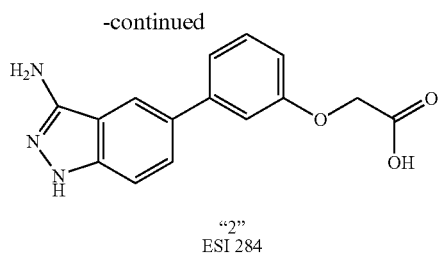

"2"
ESI 284

1. 8 ml of hydrazine hydrate are added to a solution of 22.0 g (133 mmol) of 3-cyano-4-fluorobenzoic acid in 400 ml of 1-butanol, and the mixture is heated at 110° C. for 3 hours. The reaction mixture is rendered alkaline using 1N sodium hydroxide solution and extracted with ethyl acetate. The aqueous phase is adjusted to a pH of about 4 using 1N HCl, and the precipitate formed is filtered off: 3-amino-1H-indazole-5-carboxylic acid as colourless solid; ESI 178.

2. 125 mg (0.65 mmol) of N-(3-dimethylaminopropyl)-N'-ethylcarbodiimide hydrochloride (DAPECl) are added to a solution of 88.6 mg (0.50 mmol) of 3-amino-1H-indazole-5-carboxylic acid and 70.8 mg (0.50 mmol) of 3-chlorobenzylamine in 1 ml of DMF, and the mixture is stirred at room temperature for 18 hours. The reaction mixture is added to saturated sodium hydrogencarbonate solution, and the precipitate formed is filtered off: N-(3-chlorobenzyl)-3-amino-1H-indazole-5-carboxamide ("1") as colourless solid; ESI 301.

EXAMPLE 2

The preparation of [3-(3-amino-1H-indazol-5-yl)phenoxy]acetic acid ("2") is carried out analogously to the following scheme:

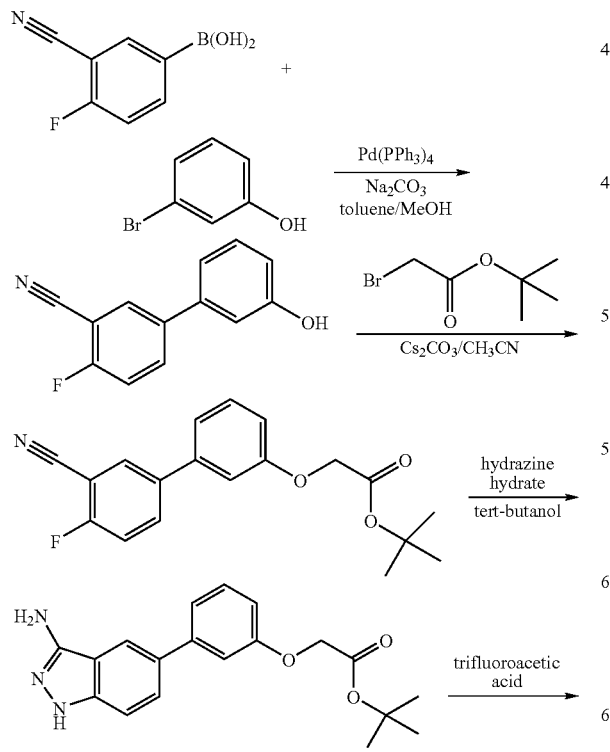

EXAMPLE 3

The preparation of N-(3-amino-1H-indazol-5-yl)-2-(3-hydroxyphenyl)acetamide hydrochloride ("3") is carried out analogously to the following scheme:

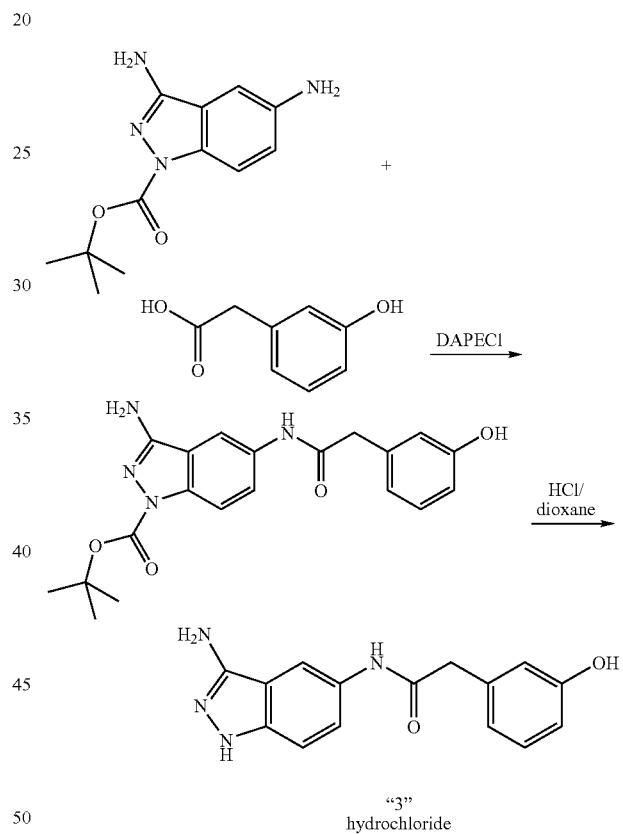

"3"
hydrochloride 1. 153 mg (0.80 mmol) of DAPECl are added to a solution of 149 mg (0.60 mmol) of tert-butyl 3,5-diaminoindazole-1-carboxylate (preparation described in WO 03/064397), 91.3 mg (0.60 mmol) of 3-hydroxyphenylacetic acid in 3 ml of DMF, and the mixture is stirred at room temperature for 18 hours. The reaction mixture is added to water, and the precipitate formed is filtered off: tert-butyl 3-amino-5-[2-(3-hydroxyphenyl)acetylamino]-indazole-1-carboxylate as colourless solid; ESI 383.

2. 10 ml of 4N HCl in dioxane are added to 110 mg (0.288 mmol) of tert-butyl (3-amino-5-[2-(3-hydroxyphenyl)acetylamino]indazole-1-carboxylate, and the mixture is stirred at room temperature for 18 hours. The reaction mixture is evaporated, digested with diethyl ether and filtered. The residue is dried: N-(3-amino-1H-indazol-5-yl)-2-(3-hydroxyphenyl)acetamide hydrochloride ("3") as colourless solid; ESI 283.

EXAMPLE 3.1

The preparation of N-(3-amino-1H-indazol-5-ylmethyl)-3-chlorobenzamide hydrochloride ("3.1") is carried out analogously to the following scheme:

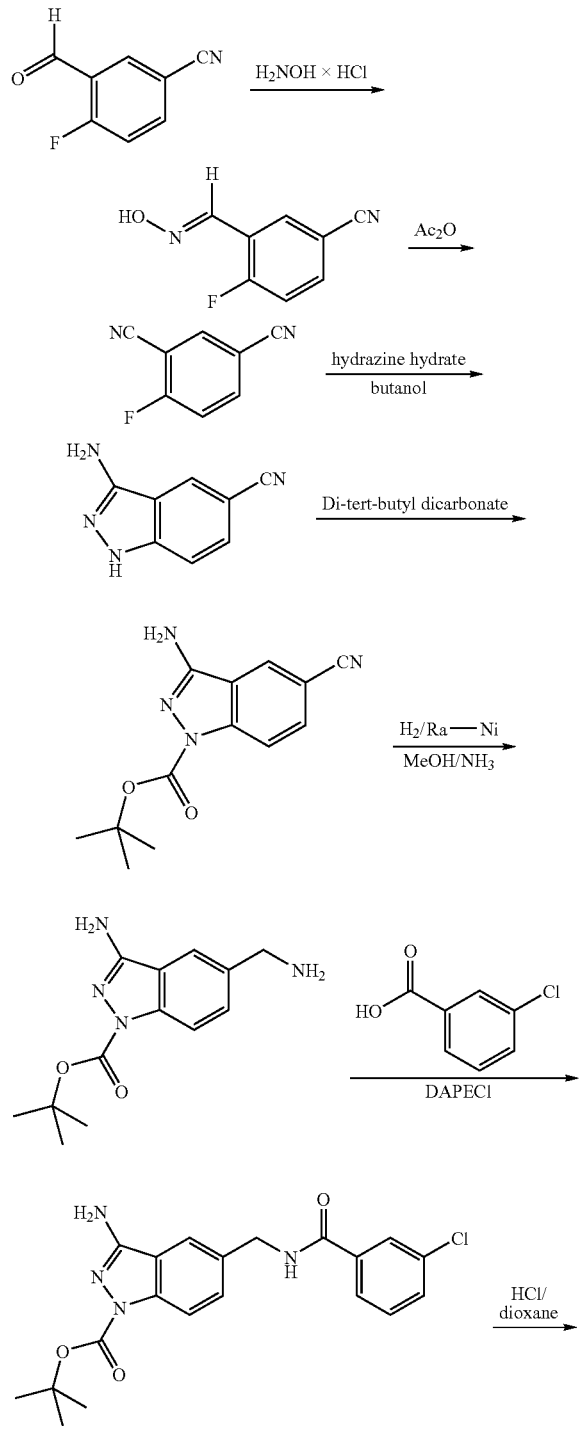

-continued

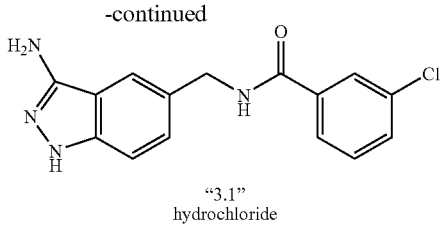

"3.1"
hydrochloride

1. A solution of 4.5 g (80 mmol) of potassium hydroxide in 20 ml of water is added to a solution of 4.0 g (58 mmol) of hydroxylammonium chloride in 20 ml of water, and the resultant solution is cooled to 0° C. 5.0 g (33.5 mmol) of 4-fluoro-3-formylbenzonitrile is slowly added to this solution with stirring. The mixture is stirred at room temperature for a further 2 hours, acetic acid is then added until a pH of 7-8 has been reached, and the solid formed is filtered off: 4-fluoro-3-(hydroxyiminomethyl)benzonitrile as colourless solid; ESI 165.

2. A solution of 5.0 g (30 mmol) of 4-fluoro-3-(hydroxyiminomethyl)benzonitrile in 40 ml of acetic anhydride is heated at the boil for 3 hours. Excess anhydride is distilled off, and the residue is partitioned between 200 ml of tert-butyl methyl ether and saturated sodium hydrogencarbonate solution. The organic phase is dried over sodium sulfate, evaporated and dissolved in diethyl ether, and petroleum ether is added. The solid formed is filtered off: 4-fluoroisophthalonitrile as colourless solid; ESI 147.

3. 4.86 ml (100 mmol) of hydrazine hydrate are added to a solution of 3.30 g (22.6 mmol) of 4-fluoroisophthalonitrile in 50 ml of 1-butanol, and the mixture is heated at 110° C. for 1 hour. The reaction mixture is allowed to cool, and 300 ml of water are added. The precipitate formed is filtered off and dried under reduced pressure: 3-amino-1H-indazole-5-carbonitrile as colourless solid; ESI 159.

4. 2.02 g (20.0 mmol) of triethylamine, 696 mg (5.70 mmol) of 4-(dimethylamino)pyridine and 4.37 g (20.0 mmol) of di-tert-butyl dicarbonate are added to a solution of 2.60 g (16.4 mmol) of 3-amino-1H-indazole-5-carbonitrile in 200 ml of THF, and the reaction mixture is stirred at room temperature for 2 hours. The majority of the THF is distilled off, and the residue is partitioned between ethyl acetate and saturated ammonium chloride solution. The organic phase is dried over sodium sulfate and evaporated, and the residue is recrystallised from tert-butyl methyl ether/petroleum ether: tert-butyl 3-amino-5-cyanoindazole-1-carboxylate as colourless solid; ESI 259.

5. 1.8 g of water-moist Raney nickel are added to a solution of 3.70 g (14.3 mmol) of tert-butyl 3-amino-5-cyanoindazole-1-carboxylate in methanolic ammonia solution, and the mixture is hydrogenated at 40° C. and a pressure of 4 bar. The catalyst is filtered off, and the filtrate is evaporated: tert-butyl 3-amino-5-aminomethylindazole-1-carboxylate as colourless solid; ESI 263.

6. 153 mg (0.80 mmol) of DAPECl are added to a solution of 157.0 mg (0.60 mmol) of tert-butyl 3-amino-5-aminomethylindazole-1-carboxylate and 93.9 mg (0.60 mmol) of 3-chlorobenzoic acid in 3 ml of DMF, and the mixture is stirred at room temperature for 18 hours. The reaction mixture is added to saturated sodium hydrogencarbonate solution, and the precipitate formed is filtered off. The residue is chromatographed on a silica-gel column using ethyl acetate as eluent:

tert-butyl 3-amino-5-[(3-chlorobenzoylamino)methyl]indazole-1-carboxylate as colourless solid, ESI 401.

7. 10 ml of 4N HCl in dioxane are added to 100 mg (0.249 mmol) of tert-butyl 3-amino-5-[(3-chlorobenzoylamino)methyl]indazole-1-carboxylate, and the mixture is left to stand at room temperature for 18 hours. The reaction mixture is evaporated and dried under reduced pressure, digested with diethyl ether and filtered. The residue is dried under reduced pressure: N-(3-amino-1H-indazol-5-ylmethyl)-3-chlorobenzamide hydrochloride ("3.1") as colourless solid; ESI 301.

EXAMPLE 4

The preparation of N-(3-amino-1H-indazol-6-yl)-2-(3-chloro-4-methoxyphenyl)acetamide ("4") is carried out analogously to the following scheme:

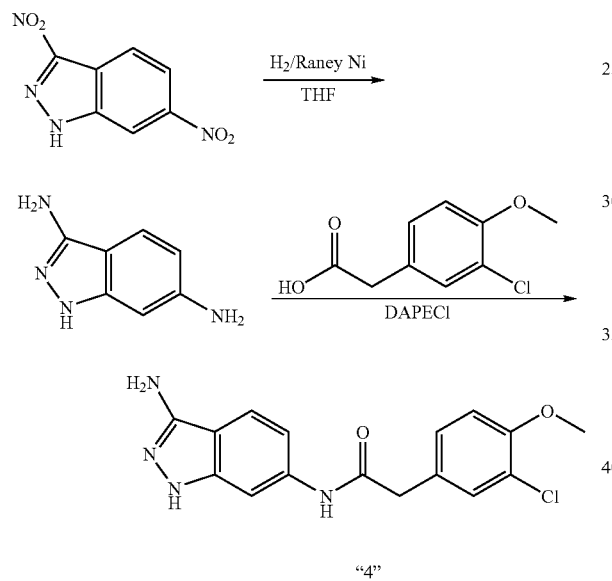

1. 340 mg of THF-moist Raney nickel are added to a solution of 1.71 g (8.22 mmol) of 3,6-dinitro-1H-indazole [prepared as described by J. Usarewicz et al., Pharmazie 47, 15 (1992)] in 100 ml of THF, and the mixture is hydrogenated at room temperature and atmospheric pressure. The catalyst is filtered off, and the filtrate is evaporated: 1H-indazole-3,6-diamine as brown solid; ESI 149.

2. 124 mg (0.65 mmol) of DAPECl are added to a solution of 47.1 mg (0.50 mmol) of 1H-indazole-3,6-diamine, 100 mg (0.50 mmol) of 3-chloro-4-methoxyphenylacetic acid in 1 ml of DMF, and the mixture is stirred at room temperature for 18 hours. The reaction mixture is added to saturated sodium hydrogencarbonate solution, and the precipitate formed is filtered off. The residue is chromatographed on a silica-gel column using ethyl acetate as eluent: N-(3-amino-1H-indazol-6-yl)-2-(3-chloro-4-methoxyphenyl)acetamide ("4") as colourless solid; ESI 331.

EXAMPLE 4.1

The preparation of N-(3-chlorobenzyl)-3-amino-1H-indazole-6-carboxamide ("4.1") is carried out analogously to the following scheme:

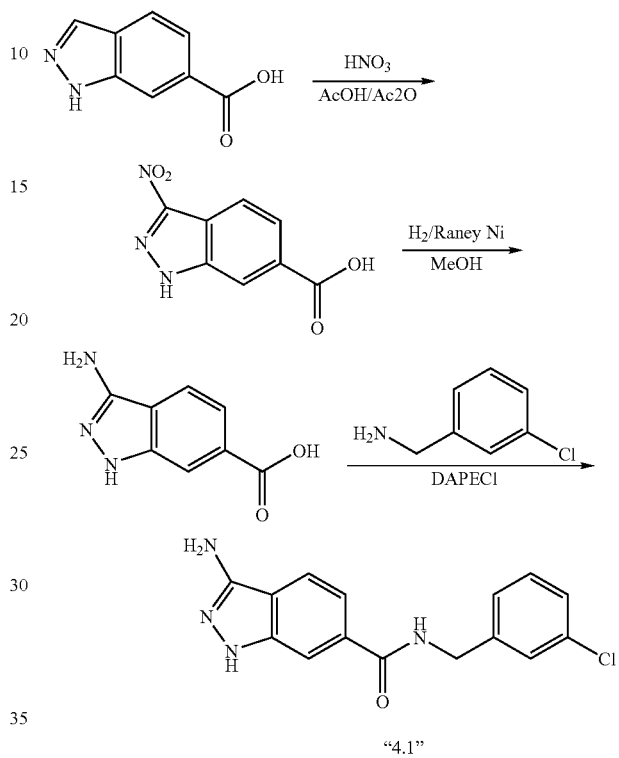

1. A solution of 4.80 g (29.6 mmol) of 1H-indazole-6-carboxylic acid (preparation described in EP 0 242 167) in 40 ml of acetic acid is warmed to 45° C. 1.95 ml (47.0 mmol) of 100% nitric acid are added dropwise to this solution. The mixture is stirred at 45° C. for one hour, 10 ml of acetic anhydride are added, and the mixture is stirred at this temperature for a further 18 hours. After the reaction mixture has been cooled to room temperature, firstly water, then 1N NaOH is added until the mixture is alkaline. After 1 hour, the mixture is acidified using conc. HCl. The precipitate formed is filtered off: 3-nitro-1H-indazole-6-carboxylic acid as yellowish solid; ESI 208.

2. 1.0 g of methanol-moist Raney nickel is added to a solution of 4.50 g (21.7 mmol) of 3-nitro-1H-indazole-6-carboxylic acid in 100 ml of methanol, and the mixture is hydrogenated at room temperature and atmospheric pressure. The catalyst is filtered off, and the filtrate is evaporated: 3-amino-1H-indazole-6-carboxylic acid as colourless solid; ESI 178.

3. 125 mg (0.65 mmol) of DAPECl are added to a solution of 88.6 mg (0.50 mmol) of 3-amino-1H-indazole-6-carboxylic acid and 70.8 mg (0.50 mmol) of 3-chlorobenzylamine in 1 ml of DMF, and the mixture is stirred at room temperature for 18 hours. The reaction mixture is added to saturated sodium hydrogencarbonate solution, and the precipitate formed is filtered off: N-(3-chlorobenzyl)-3-amino-1H-indazole-6-carboxamide ("4.1") as colourless solid: ESI 301.

EXAMPLE 5

The preparation of 6-(4-phenoxyphenyl)-1H-indazol-3-ylamine ("5") is carried out analogously to the following scheme:

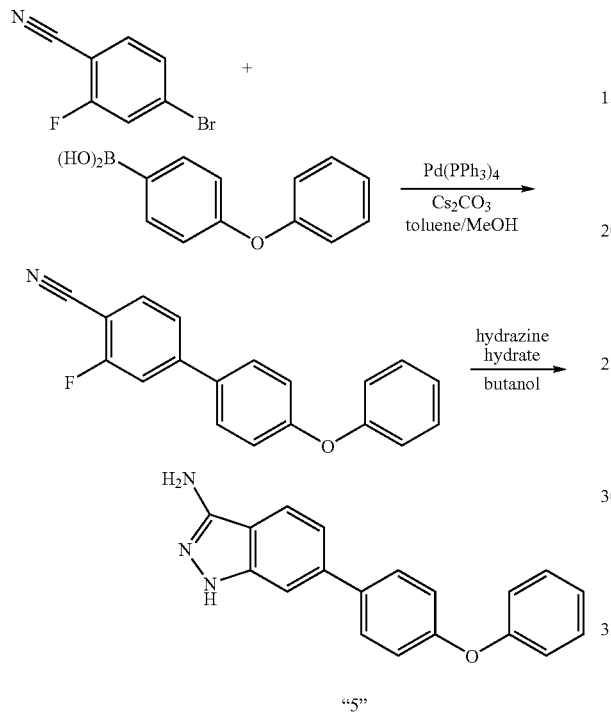

EXAMPLE 6

The preparation of 5-(3-methanesulfonylphenyl)-1H-indazol-3-ylamine ("6") is carried out analogously to the following scheme:

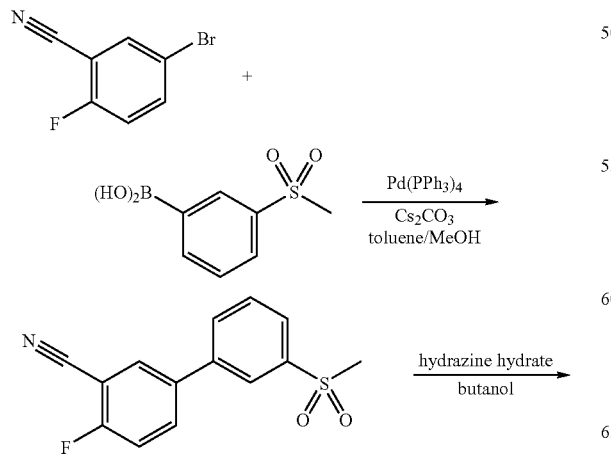

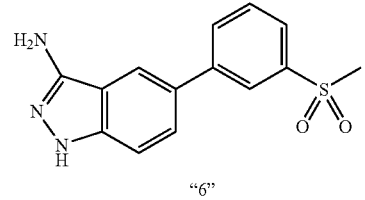

EXAMPLE 6.1

The preparation of 6-(3-chloro-4-methoxybenzyloxy)-1H-indazol-3-ylamine ("6.1") is carried out analogously to the following scheme:

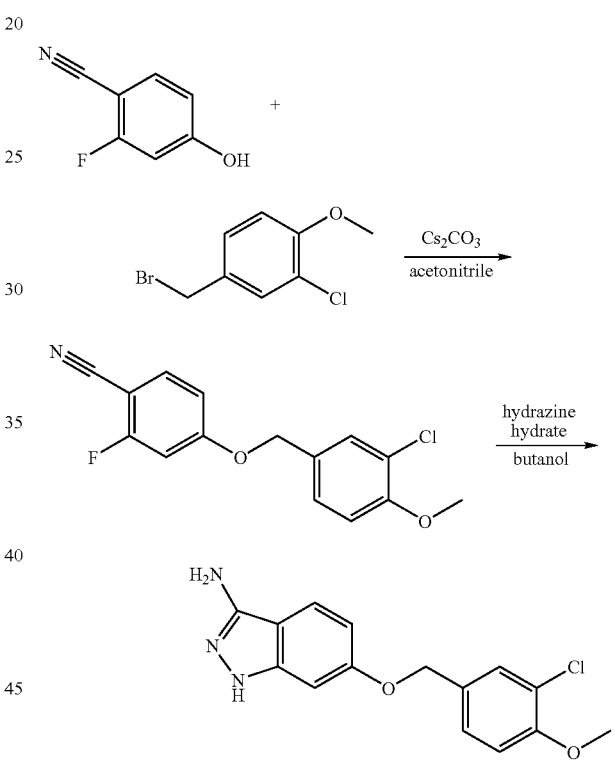

EXAMPLE 6.2

The preparation of N5-(3-chloro-4-methoxybenzyl)-1H-indazole-3,5-diamine ("6.2") and N5,N5-bis(3-chloro-4-methoxybenzyl)-1H-indazole-3,5-diamine ("6.2a") is carried out analogously to the following scheme:

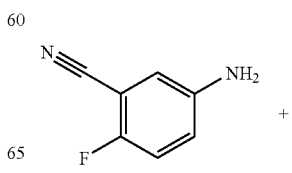

-continued
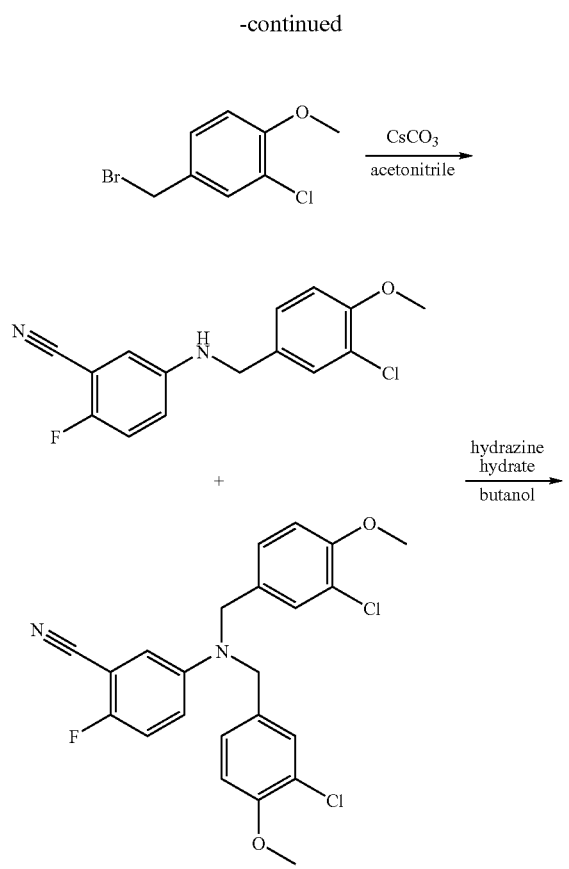
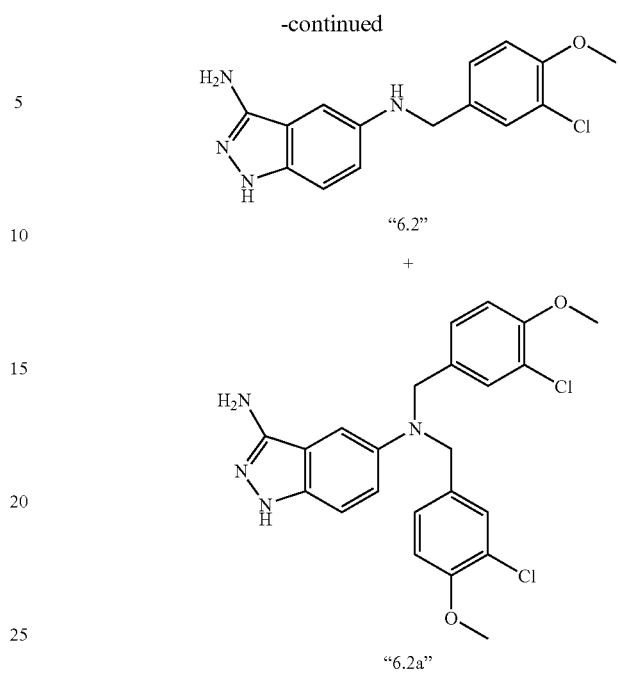
"6.2"
+
"6.2a"
The two compounds are separated by preparative thin-layer chromatography (Si60, ethyl acetate/methanol 9:1).
EXAMPLE 6.3
The preparation of 1-(3-amino-1H-indazol-5-yl)-3-(4-benzyloxyphenyl)urea ("6.3") is carried out analogously to the following scheme:
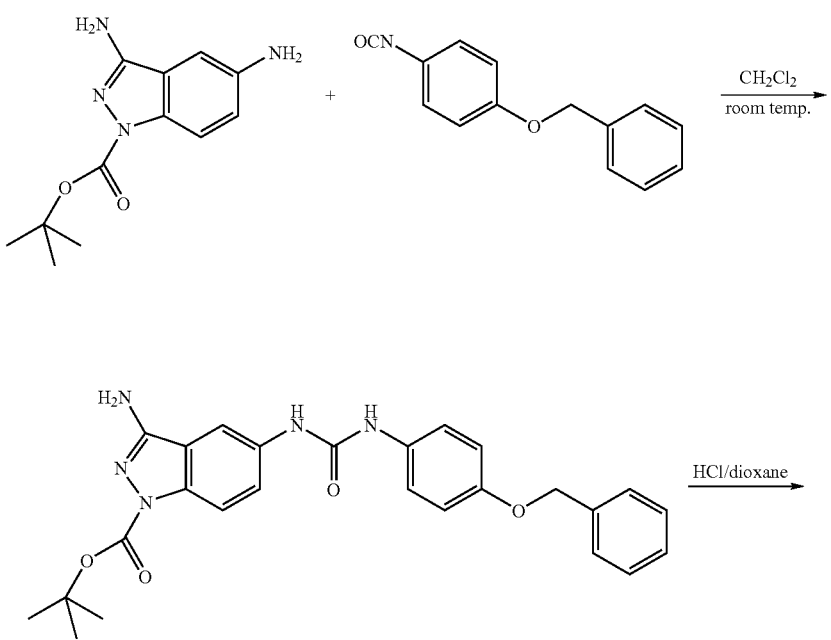

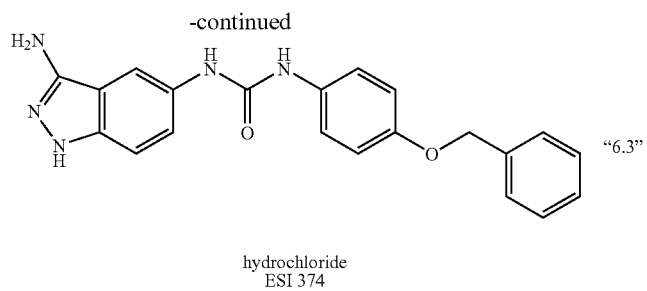

hydrochloride
ESI 374

The compound 1-(3-amino-1H-indazol-5-yl)-3-(3-chlorophenyl)urea ("6.3a"), hydrochloride, is obtained analogously; ESI 302.

EXAMPLE 7

The preparation of (E)-3-(3-amino-1H-indazol-5-yl)-N-(3-hydroxybenzyl)acrylamide ("162") is carried out analogously to the following scheme:

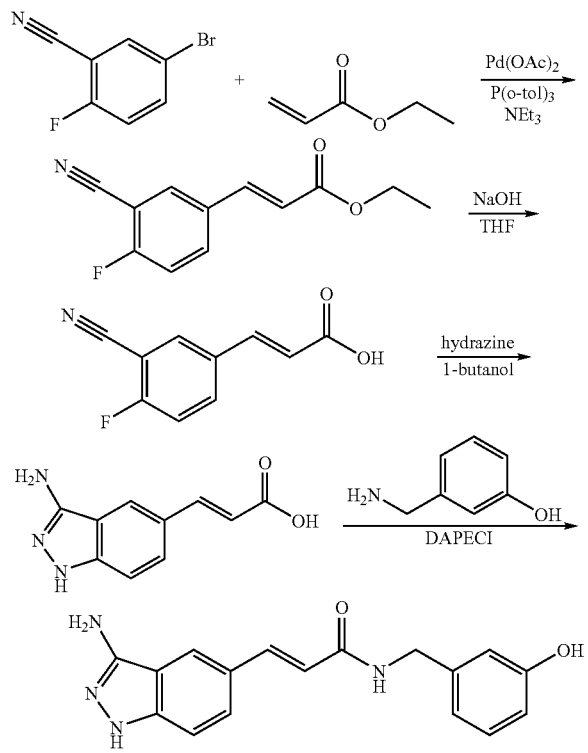

1. 5.50 ml of ethyl acrylate, 500 mg (2.2 mmol) of palladium (II) acetate, 500 mg (2.2 mmol) of tri-o-tolylphosphine and 14 ml of triethylamine are added to a solution of 10.0 g (50.0 mmol) of 5-bromo-2-fluorobenzonitrile in 70 ml of acetonitrile, and the mixture is heated at the boil for 2 days under nitrogen. After the reaction mixture has been cooled to room temperature, water is added, and the mixture is extracted three times with toluene. The combined organic phases are dried over sodium sulfate and evaporated: ethyl 3-(3-cyano-4-fluorophenyl)acrylate as colourless solid, ESI 220.

2. 60 ml of 1N aqueous sodium hydroxide solution are added to a solution of 10.9 g (49.8 mmol) of ethyl 3-(3-cyano-4-fluorophenyl)acrylate in 200 ml of THF, and the reaction mixture is stirred at room temperature for 2 days. The THF is distilled off, the aqueous residue is acidified using conc. HCl, and the mixture is extracted with ethyl acetate. The organic phase is dried over sodium sulfate and evaporated: 3-(3-cyano-4-fluorophenyl)acrylic acid as colourless solid, ESI 192.

3. 10 ml (206 mmol) of hydrazinium hydroxide are added to a solution of 6.40 g (33.5 mmol) of 3-(3-cyano-4-fluorophenyl)acrylic acid, and the mixture is heated at 100° C. for 3 hours. The reaction mixture is evaporated to a volume of about 20 ml under reduced pressure, and water is added. The precipitate formed is filtered off and dried: 3-(3-amino-1H-indazol-5-yl)acrylic acid as colourless solid, ESI 204.

4. 287 mg (1.50 mmol) of N-(3-dimethylaminopropyl)-N'-ethylcarbodiimide hydrochloride (DAPECl) are added to a solution of 203 mg (1.00 mmol) of 3-(3-amino-1H-indazol-5-yl)acrylic acid and 123 mg (1.00 mmol) of 3-hydroxybenzylamine in 2 ml of DMF, and the mixture is stirred at room temperature for 18 hours. Water and 1N HCl are added to the reaction mixture, which is extracted with ethyl acetate. The organic phase is dried over sodium sulfate and evaporated, and the residue is chromatographed on a silica-gel column using ethyl acetate/methanol 9:1, giving 3-(3-amino-1H-indazol-5-yl)-N-(3-hydroxybenzyl)acrylamide ("162") as colourless solid, ESI 309.

EXAMPLE 8

The preparation of 3-(3-amino-1H-indazol-5-yl)-N-(3-chlorobenzyl)propionamide ("163") is carried out analogously to the following scheme:

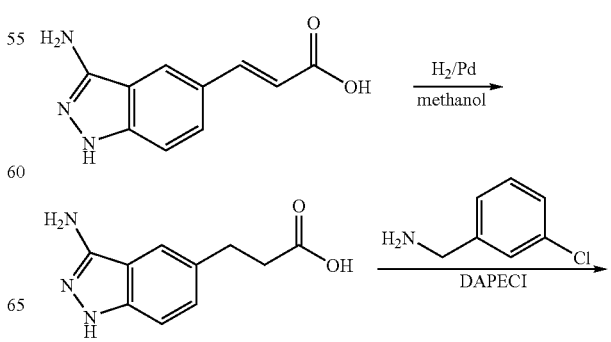

-continued

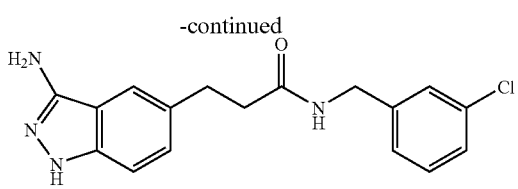

EXAMPLE 9

The preparation of 5-(5-trifluoromethyl-1H-imidazol-2-yl)-1H-indazol-3-ylamine ("164") is carried out analogously to the following scheme:

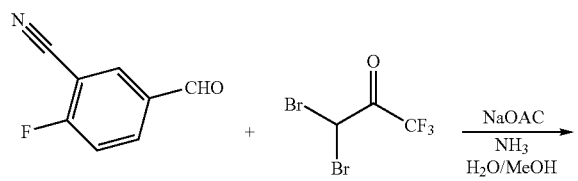

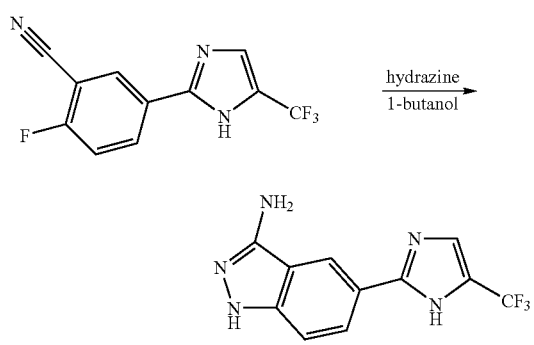

1. 16.2 g (60.0 mmol) of 1,1-dibromo-3,3,3-trifluoroacetone are mixed with 68 ml of water, and 16.3 g (120 mmol) of sodium acetate trihydrate are added. This solution is heated to 90° C. and added in one portion to a pre-prepared suspension of 8.95 g (60.0 mmol) of 2-fluoro-4-formylbenzonitrile in 300 ml of methanol and 84 ml of conc. ammonia. The reaction mixture is stirred at room temperature for 40 hours. It is concentrated to a volume of about 200 ml, and the precipitate formed is filtered off: crude 2-fluoro-5-(5-trifluoromethyl-1H-imidazol-2-yl)benzonitrile as yellow-brown solid (ESI 256), which is employed without further purification for subsequent reactions.

2. 1.17 ml (24 mmol) of hydrazinium hydroxide are added to a solution of 2.00 g of 2-fluoro-5-(5-trifluoromethyl-1H-imidazol-2-yl)benzonitrile (about 50%, about 3.9 mmol) in 20 ml of 1-butanol, and the mixture is heated at 100° C. for 3 hours. The reaction mixture is evaporated, and the residue is taken up in ethyl acetate. The precipitate formed is filtered off and dried: 5-(5-methyl-1H-imidazol-2-yl)-1H-indazol-3-ylamine ("164") as yellow solid, ESI 268.

EXAMPLE 10

The preparation of N'-[1-(3-amino-1H-indazol-5-yl)meth(E)ylidene]-(3-chlorophenyl)acetohydrazide ("165") is carried out analogously to the following scheme:

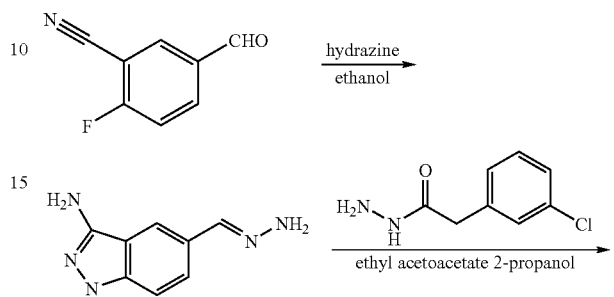

9.0 ml (185 mmol) of hydrazinium hydroxide are added to a suspension of 2.00 g (13.4 mmol) of 3-cyano-4-fluorobenzaldehyde in 10 ml of ethanol, and the mixture is heated at 60° C. for 5 hours. Ethanol is distilled off, and the residue is left in the refrigerator for 14 hours. The crystals formed are filtered off: 5-hydrazonomethyl-1H-indazol-3-ylamine as yellowish crystals; ESI 176.

A solution of 300 mg (1.71 mmol) of hydrazonomethyl-1H-indazol-3-ylamine, 318 mg (1.72 mmol) of (3-chlorophenyl)acetohydrazide and 224 mg (1.72 mmol) of ethyl acetoacetate in 10 ml of 2-propanol is heated at 80° C. for 10 hours. The reaction mixture is evaporated and chromatographed on a silica-gel column using dichloromethane/methanol 8:2 as eluent: N'-[1-(3-amino-1H-indazol-5-yl)meth(E)ylidene]-(3-chlorophenyl)acetohydrazide ("165") as yellowish solid; ESI 328.

EXAMPLE 11

The preparation of 5-(5-methyl-1H-imidazol-2-yl)-1H-indazol-3-ylamine ("166") is carried out analogously to the following scheme:

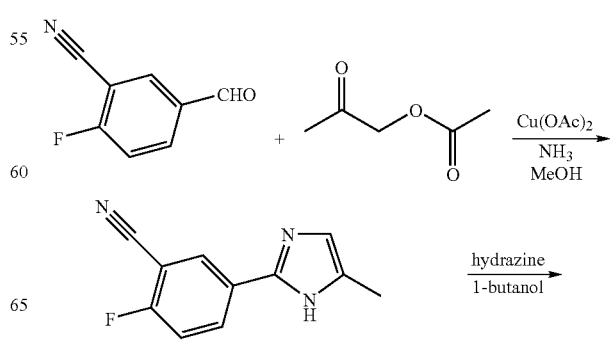

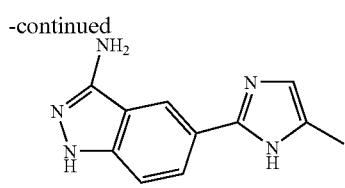

EXAMPLE 12

The preparation of 5-(3-amino-1H-indazol-5-yl)furan-2-carboxylic acid ("167") is carried out analogously to the following scheme:

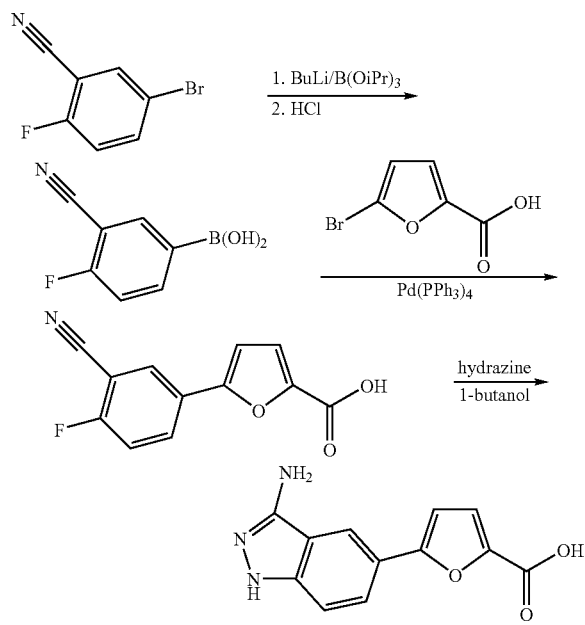

1. A solution of 5.00 g (25.0 mmol) of 5-bromo-2-fluorobenzonitrile and 5.64 g (30.0 mmol) of triisopropyl borate in a mixture of 10 ml of THF and 40 ml of toluene is cooled to −70° C. under nitrogen. 12 ml of a 15% solution of n-butyllithium in hexane (30 mmol) are added dropwise over the course of one hour at this temperature. The reaction mixture is slowly warmed to −20° C., and 25 ml of 1N HCl are then added. After warming to room temperature, the organic phase is separated off, dried over sodium sulfate and evaporated. The solid residue is taken up in tert-butyl methyl ether, and the precipitate is filtered and dried: 3-cyano-4-fluorobenzeneboronic acid as colourless solid, ESI 166.

2. 260 mg (0.23 mmol) of tetrakis(triphenylphosphine)palladium(0) are added under nitrogen to a solution of 1.30 g (7.88 mmol) of 3-cyano-4-fluorobenzeneboronic acid and 1.62 g (8.50 mmol) of 5-bromo-2-furanoic acid in a mixture of 10 ml of toluene and 8 ml of THF, and a solution of 1.40 g (16.7 mmol) of sodium hydrogencarbonate in 10 ml of water is added. The reaction mixture is heated at the boil for 3 hours with vigorous stirring. After cooling, the reaction mixture is partitioned between water and ethyl acetate. The aqueous phase is acidified using conc. HCl and extracted with ethyl acetate. The organic phase is dried over sodium sulfate and evaporated: 5-(3-cyano-4-fluorophenyl)furan-2-carboxylic acid as yellowish solid, ESI 232.

3. 1.85 g (37.0 mmol) of hydrazinium hydroxide are added to a solution of 870 mg (3.76 mmol) of 5-(3-cyano-4-fluorophenyl)furan-2-carboxylic acid in 20 ml of 1-butanol, and the mixture is heated at 80° C. for 12 hours. The precipitate formed is filtered off and washed with methanol: 5-(3-amino-1H-indazol-5-yl)furan-2-carboxylic acid as colourless solid, ESI 244.

EXAMPLE 13

The preparation of 2-(3-amino-1H-indazol-6-yl)oxazole-4-carboxylic acid ("168") is carried out analogously to the following scheme:

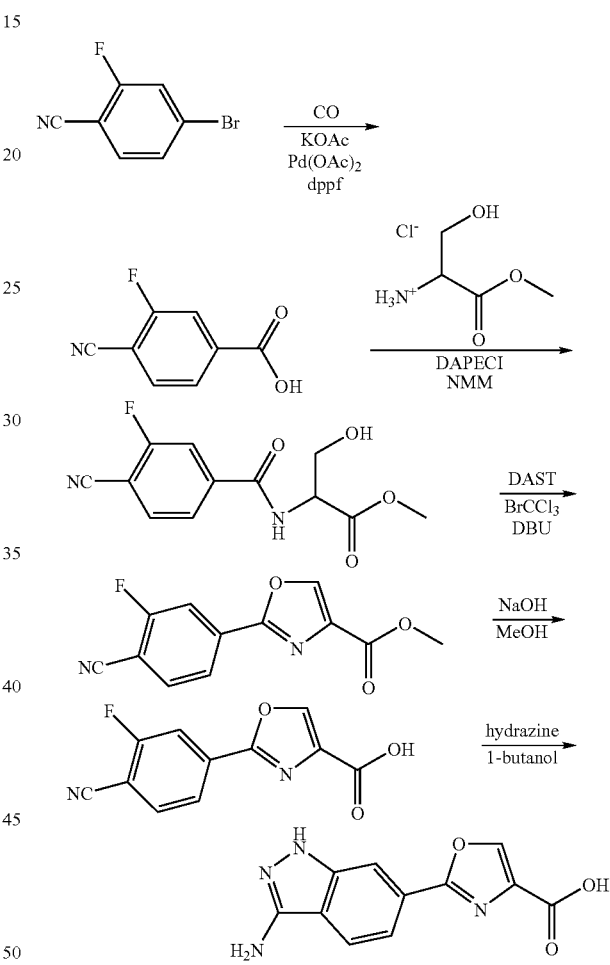

EXAMPLE 14

The preparation of [5-(3-amino-1H-indazol-6-yl)furan-2-yl]methanol ("169") is carried out analogously to the following scheme:

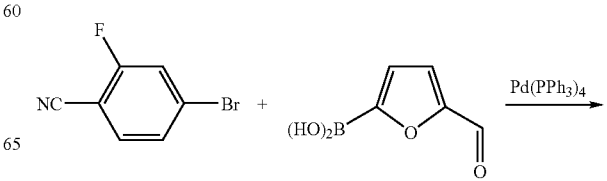

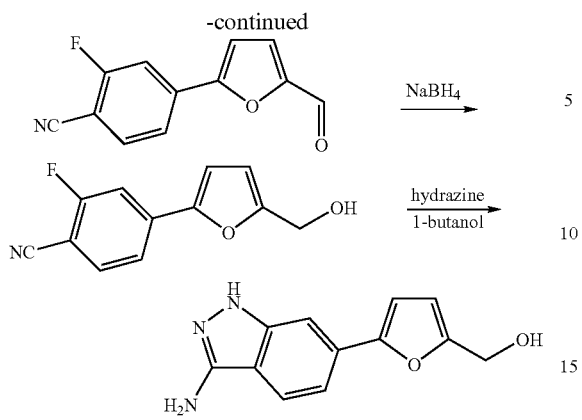

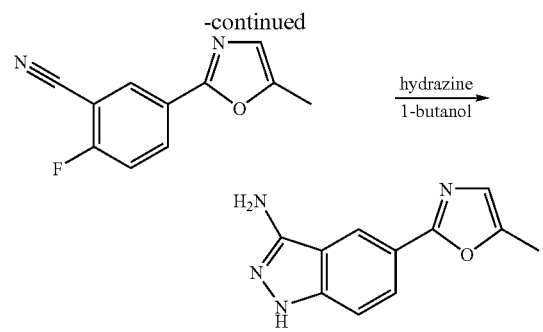

EXAMPLE 15

The preparation of 6-(5-methyloxazol-2-yl)-1H-indazol-3-ylamine ("170") is carried out analogously to the following scheme:

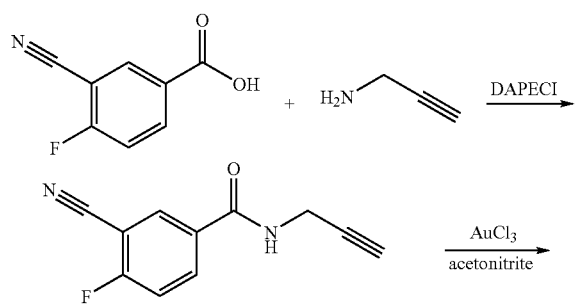

1. 4.53 g (23.6 mmol) of N-(3-dimethylaminopropyl)-N'-ethylcarbodiimide hydrochloride (DAPECl) and 2.78 g (18.2 mmol) of 1-hydroxybenzotriazole hydrate are added to a solution of 3.00 g (18.2 mmol) of 3-cyano-4-fluorobenzoic acid and 1.01 g (18.2 mmol) of propargylamine in 10 ml of DMF, and the mixture is stirred at room temperature for 18 hours. Water is added to the reaction mixture, and the precipitate formed is filtered off: 3-cyano-4-fluoro-N-prop-2-ynyl-benzamide as brownish solid, ESI 203.

2. A solution of 2.10 g (10.4 mmol) of 3-cyano-4-fluoro-N-prop-2-ynylbenzamide and 315 mg (1.04 mmol) of gold(III) chloride in 20 ml of acetonitrile is stirred at room temperature for 18 hours. The reaction mixture is filtered, and the filtrate is evaporated: 2-fluoro-5-(5-methyloxazol-2-yl)benzonitrile as brownish solid, ESI 203.

3. 120 µl (2.4 mmol) of hydrazinium hydroxide are added to a solution of 100 mg (0.495 mmol) of 2-fluoro-5-(5-methyloxazol-2-yl)benzonitrile in 1 ml of 1-butanol, and the mixture is heated at 100° C. for 12 hours. The reaction mixture is evaporated, and the residue is purified by preparative HPLC: 5-(5-methyloxazol-2-yl)-1H-indazol-3-ylamine ("170") as colourless solid; ESI 215.

The following compounds are obtained analogously

| No. | Structural formula | ESI | Preparation analogous to Example No. |
|---|---|---|---|
| 7 | ![structure] | 268 | 6 |
| 8 | ![structure] | 288 | 6 |
| 9 | ![structure] | 332 | 1 |

-continued

| No. | Structural formula | ESI | Preparation analogous to Example No. |
|---|---|---|---|
| 10 | 3-amino-1H-indazole-5-carboxylic acid N'-(3-chlorophenyl)hydrazide | 303 | 1 |
| 11 | N-(3-amino-1H-indazol-5-yl)-2-(3-chloro-4-hydroxyphenyl)acetamide | 318 | 3 |
| 12 | N-(3-amino-1H-indazol-5-yl)-2-(benzo[1,2,5]thiadiazol-5-yl)acetamide | 325 | 3 |
| 13 | 3-amino-N-(3-hydroxybenzyl)-1H-indazole-5-carboxamide | 283 | 1 |
| 14 | 3-amino-N-(benzo[1,2,5]thiadiazol-5-ylmethyl)-1H-indazole-5-carboxamide |  | 1 |
| 15 | 3-amino-N-(4-hydroxy-2-methylbenzyl)-1H-indazole-5-carboxamide |  | 1 |
| 16 | 3-amino-N-(3-methoxybenzyl)-1H-indazole-5-carboxamide |  | 1 |
| 17 | 3-amino-5-phenyl-1H-indazole | 210 | 5 |
| 18 | [4-(3-amino-1H-indazol-5-yl)phenoxy]acetic acid | 284 | 2 |

-continued

| No. | Structural formula | ESI | Preparation analogous to Example No. |
|---|---|---|---|
| 19 | | 298 | 6 |
| 20 | | 217 | 5, 6 |
| 21 | | 240 | 5, 6 |
| 22 | | 199 | 5, 6 |
| 23 | | 275 | 6.1 |
| 24 | | 254 | 6.1 |
| 25 | | 226 | 5 |

-continued

| No. | Structural formula | ESI | Preparation analogous to Example No. |
|---|---|---|---|
| 26 | | 210 | 5 |
| 27 | | 240 | 5 |
| 28 | | 240 | 6 |
| 29 | | 294 | 6 |
| 30 | | 228 | 6 |
| 31 | | 228 | 6 |
| 32 | | 302 | 6 |
| 33 | | 240 | 5 |

-continued
| No. | Structural formula | ESI | Preparation analogous to Example No. |
|---|---|---|---|
| 34 | 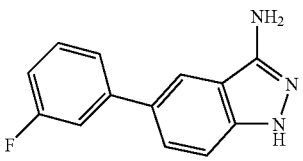 | 228 | 6 |
| 35 | 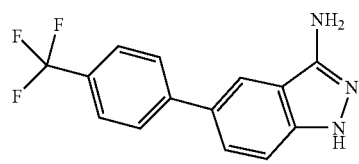 | 278 | 6 |
| 36 | 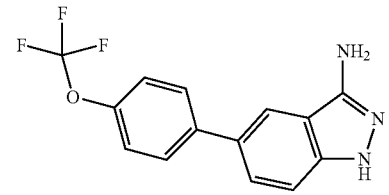 | 294 | 6 |
| 37 | 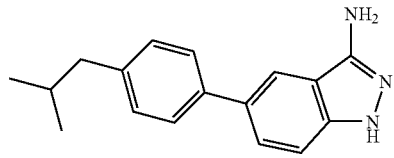 | 26 | 6 |
| 38 | 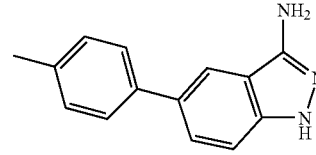 | 224 | 6 |
| 39 | 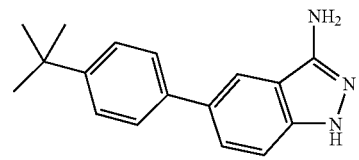 | 266 | 6 |
| 40 | 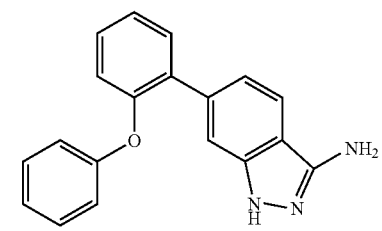 | 302 | 5 |
| 41 | 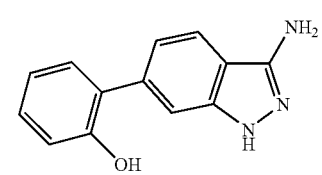 | 226 | 5 |

-continued

| No. | Structural formula | ESI | Preparation analogous to Example No. |
|---|---|---|---|
| 42 | 6-(3-(trifluoromethyl)phenyl)-1H-indazol-3-amine | 278 | 5 |
| 43 | 6-(3-fluorophenyl)-1H-indazol-3-amine | 228 | 5 |
| 44 | 6-(3-butoxyphenyl)-1H-indazol-3-amine | 282 | 5 |
| 45 | 6-(4-fluorophenyl)-1H-indazol-3-amine | 228 | 5 |
| 46 | 6-(4-(trifluoromethyl)phenyl)-1H-indazol-3-amine | 278 | 5 |
| 47 | 6-(3-methylphenyl)-1H-indazol-3-amine | 224 | 5 |
| 48 | 6-(2-methylphenyl)-1H-indazol-3-amine | 224 | 5 |
| 49 | 6-(benzo[d][1,3]dioxol-5-yl)-1H-indazol-3-amine | 254 | 5 |
| 50 | 6-(4-(ethylsulfonyl)phenyl)-1H-indazol-3-amine | 278 | 5 |

-continued

| No. | Structural formula | ESI | Preparation analogous to Example No. |
|---|---|---|---|
| 51 | 2-(trifluoromethyl)phenyl-6-(1H-indazol-3-amine) | 278 | 5 |
| 52 | 4-isobutylphenyl-6-(1H-indazol-3-amine) | 266 | 5 |
| 53 | 4-methylphenyl-6-(1H-indazol-3-amine) | 224 | 5 |
| 54 | 4-tert-butylphenyl-6-(1H-indazol-3-amine) | 266 | 5 |
| 55 | 4-hydroxyphenyl-5-(1H-indazol-3-amine) | 226 | 6 |
| 56 | 3-hydroxyphenyl-5-(1H-indazol-3-amine) | 226 | 6 |
| 57 | 2-hydroxyphenyl-5-(1H-indazol-3-amine) | 226 | 6 |
| 58 | 3-hydroxyphenyl-6-(1H-indazol-3-amine) | 226 | 5 |

| No. | Structural formula | ESI | Preparation analogous to Example No. |
|-----|-------------------|-----|--------------------------------------|
| 59 | | 278 | 6 |
| 60 | | 224 | 6 |
| 61 | | 268 | 6 |
| 62 | | 302 | 6 |
| 63 | | 287 | 5 |
| 64 | | 294 | 5 |
| 65 | | 298 | 6 |
| 66 | | 340 | 6 |

| No. | Structural formula | ESI | Preparation analogous to Example No. |
|---|---|---|---|
| 67 | | 298 | 6 |
| 68 | | 298 | 6 |
| 69 | | 340 | 6 |
| 70 | | 340 | 5 |
| 71 | | 284 | 2 |
| 72 | | 284 | 5 |

-continued

| No. | Structural formula | ESI | Preparation analogous to Example No. |
|---|---|---|---|
| 73 | | 240 | 5 |
| 74 | | 226 | 5 |
| 75 | | 268 | 5 |
| 76 | | 240 | 6 |
| 77 | | 286 | 5 |
| 78 | | 267 | 6 |
| 79 | | 253 | 6 |
| 80 | | 278 | 6 |

-continued

| No. | Structural formula | ESI | Preparation analogous to Example No. |
|---|---|---|---|
| 81 | | 282 | 6 |
| 82 | | 286 | 6 |
| 83 | | 268 | 6 |
| 84 | | 254 | 6 |
| 85 | | 288 | 6 |
| 86 | | 240 | 6 |
| 87 | | 302 | 6 |
| 88 | | 288 | 6 |

| No. | Structural formula | ESI | Preparation analogous to Example No. |
|---|---|---|---|
| 89 | | 288 | 5 |
| 90 | | 240 | 5 |
| 91 | | 253 | 5 |
| 92 | | 225 | 5 |
| 93 | | 254 | 5 |
| 94 | | 228 | 5 |
| 95 | | 302 | 5 |
| 96 | | 254 | 5 |
| 97 | | 331 | 1 |

-continued

| No. | Structural formula | ESI | Preparation analogous to Example No. |
|---|---|---|---|
| 98 | | 321 | 3 |
| 99 | | 297 | 1 |
| 100 | | 369 | 1 |
| 101 | | 319 | 1 |
| 102 | | 317 | 1 |
| 103 | | 311 | 1 |
| 104 | | 247 | 1 |

-continued

| No. | Structural formula | ESI | Preparation analogous to Example No. |
|---|---|---|---|
| 105 | | 331 | 3 |
| 106 | | 339 | 3 |
| 107 | | 304 | 3 |
| 108 | | 293 | 3 |
| 109 | | 304 | 3 |
| 110 | | 331 | 3 |
| 111 | | 335 | 1 |

-continued

| No. | Structural formula | ESI | Preparation analogous to Example No. |
|---|---|---|---|
| 112 | | 346 | 3 |
| 113 | | 301 | 4.1 |
| 114 | | 285 | 3 |
| 115 | | 336 | 1 |
| 116 | x HCl | 283 | 3 |
| 117 | | 335 | 1 |
| 118 | x 2 HCl | 308 | 1 |

-continued

| No. | Structural formula | ESI | Preparation analogous to Example No. |
|---|---|---|---|
| 119 | 3-amino-1H-indazole-5-carboxylic acid (4-hydroxybenzyl)amide | 283 | 1 |
| 120 | 1-(3-amino-1H-indazol-5-yl)-3-(2,5-dichlorophenyl)urea × HCl | 336 | 6.3 |
| 121 | 1-(3-amino-1H-indazol-5-yl)-3-(2-chlorophenyl)urea × HCl | 302 | 6.3 |
| 122 | N-(3-amino-1H-indazol-5-yl)-2-(3-chlorophenyl)acetamide × HCl | 301 | 3 |
| 123 | N-(3-amino-1H-indazol-5-yl)-2-(2-chlorophenyl)acetamide × HCl | 301 | 3 |
| 124 | 1-(3-amino-1H-indazol-5-yl)-3-(4-hydroxyphenyl)urea × HCl | 284 | 6.3 subsequently H₂/Pd |
| 125 | 3-amino-1H-indazole-5-carboxylic acid N'-(2-chlorophenyl)hydrazide | 302 | 1 |

-continued

| No. | Structural formula | ESI | Preparation analogous to Example No. |
|---|---|---|---|
| 126 | [3-amino-1H-indazol-5-yl amide of 3-(4-hydroxyphenyl)propanoic acid] x HCl | 297 | 3 |
| 127 | 3-amino-N-(2,5-dichlorobenzyl)-1H-indazole-5-carboxamide | 335 | 1 |
| 128 | [3-amino-N-((3-amino-1H-indazol-5-yl)methyl)-1H-indazole-5-carboxamide] x 2 HCl | 322 | 3.1 |
| 129 | [3-amino-N-((3-amino-1H-indazol-5-yl)methyl)-1H-indazole-6-carboxamide] x 2 HCl | 322 | 3.1 |
| 130 | [N-((3-amino-1H-indazol-5-yl)methyl)-4-hydroxybenzamide] x 2 HCl | 283 | 3.1 |
| 131 | N-((3-amino-1H-indazol-5-yl)methyl)-3-hydroxybenzamide | 283 | 3.1 |
| 132 | 3-amino-N-((1S)-1-(3-methoxyphenyl)ethyl)-1H-indazole-5-carboxamide | 311 | 1 |

| No. | Structural formula | ESI | Preparation analogous to Example No. |
|---|---|---|---|
| 133 | | 311 | 1 |
| 134 | x HCl | 281 | 3 |
| 135 | | 285 | 1 |
| 136 | | 296 | 1 |
| 137 | | 286 | 1 |
| 138 | | 281 | 1 |
| 139 | | 311 | 1 |

-continued

| No. | Structural formula | ESI | Preparation analogous to Example No. |
|---|---|---|---|
| 140 | | 345 | 1 |
| 141 | x HCl | 301 | 1 |
| 142 | | 315 | 1 |
| 143 | | 315 | 1 |
| 144 | | 311 | 1 |
| 145 | | 299 | 3 |
| 146 | | 325 | 1 |

| No. | Structural formula | ESI | Preparation analogous to Example No. |
|---|---|---|---|
| 147 | | 268 | 1 |
| 148 | | 268 | 1 |
| 149 | | 283 | 1 |
| 150 | x 2 HCl | 283 | amine component BOC-protected; 1; then HCl/dioxane |
| 151 | | 422 | 1 |
| 152 | | 297 | 1 |
| 153 | | | |
| 154 | | | |

-continued

| No. | Structural formula | ESI | Preparation analogous to Example No. |
|---|---|---|---|
| 155 | | | |
| 156 | | | |
| 157 | | | |
| 158 | | | from "133" using BBr₃ |
| 159 | | | |
| 160 | | | from "144" using BBr₃ |
| 161 | | | |
| 171 | | 311 | 1 |

-continued
| No. | Structural formula | ESI | Preparation analogous to Example No. |
|---|---|---|---|
| 172 | 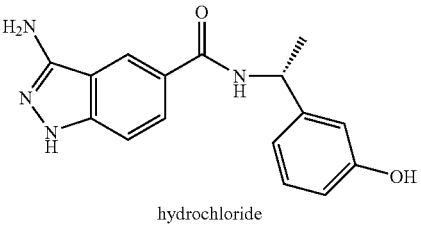 hydrochloride | 297 | 1 |
| 173 | 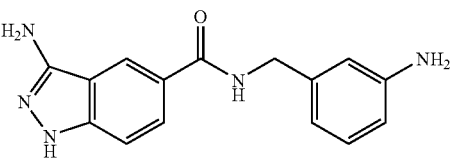 | 282 | 1 |
| 174 | 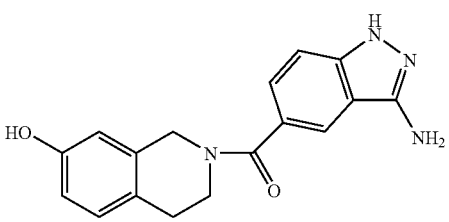 | 309 | 1 |
| 175 | 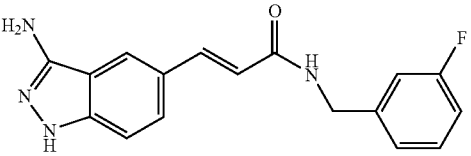 | 311 | 7 |
| 176 | 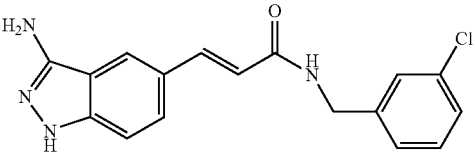 | 327 | 7 |
| 177 | 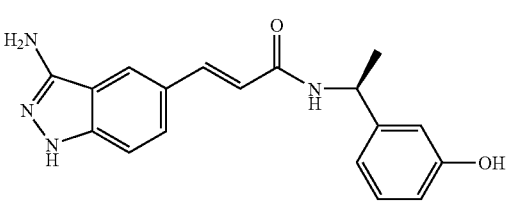 | 323 | 7 |
| 178 | 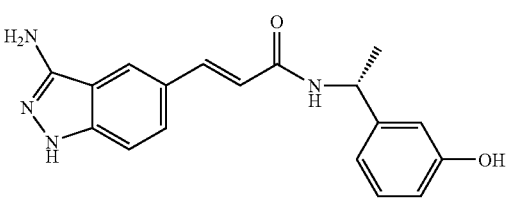 | 323 | 7 |

-continued

| No. | Structural formula | ESI | Preparation analogous to Example No. |
|---|---|---|---|
| 179 | (3-amino-1H-indazol-5-yl acrylamide with N-(2-hydroxybenzyl), hydrobromide) | 309 | from "181" by reaction with BBr₃ |
| 180 | (4-hydroxybenzyl acrylamide with 3-amino-1H-indazol-5-yl) | 309 | 7 |
| 181 | (3-amino-1H-indazol-5-yl acrylamide with N-(2-methoxybenzyl)) | 323 | 7 |
| 182 | (bis-(3-amino-1H-indazol-5-yl) acrylamide), dihydrochloride | 348 | 1. Analogously to Ex. 7 (amine component BOC-protected) 2. HCl/dioxane |
| 183 | (3-amino-1H-indazol-5-yl acrylamide with 4-(pyridin-4-ylmethyl)phenyl) | 370 | 7 |
| 184 | (3-amino-1H-indazol-5-yl acrylamide with N-(pyridin-4-ylmethyl)) | 294 | 7 |
| 185 | (3-amino-1H-indazole-5-carboxamide with 4-(pyridin-4-ylmethyl)phenyl) | 344 | 1 |
| 186 | (3-amino-1H-indazol-5-yl acrylamide with N-(2-(piperidin-4-yloxy)benzyl)) | 392 | 1. Analogously to Ex. 7 (amine component BOC-protected) 2. HCl/dioxane |

-continued

| No. | Structural formula | ESI | Preparation analogous to Example No. |
|---|---|---|---|
| 187 | | 294 | 7 |
| 188 | dihydrochloride | 366 | 1. Analogously to Ex. 1 (amine component BOC-protected)<br>2. HCl/dioxane |
| 189 | | 323 | 7 |
| 190 | | 351 | 7 |
| 191 | | 329 | 7 |
| 192 | hydrochloride | 327 | 7 |
| 193 | | 337 | 7 |

-continued

| No. | Structural formula | ESI | Preparation analogous to Example No. |
|---|---|---|---|
| 194 | (structure) | 341 | 7 |
| 195 | (structure) | 310 | 10 |
| 196 | (structure) | 324 | 10 |
| 197 | (structure) | 260 | 12 |
| 198 | (structure) | 244 | 12 |
| 199 | (structure) hydrochloride | 347 | 3.1 |
| 200 | (structure) | 215 | 15 |
| 201 | (structure) | 258 | from "167" using methanol/chlorotrimethylsilane |

The following examples relate to pharmaceutical preparations:

EXAMPLE A

Injection Vials

A solution of 100 g of an active ingredient according to the invention and g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient according to the invention with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient according to the invention, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient according to the invention are mixed with 99.5 g of Vaseline under aseptic conditions.

EXAMPLE E

Tablets

A mixture of 1 kg of active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient according to the invention are introduced into hard gelatine capsules in a conventional manner in such a way that each capsule contains 20 mg of the active ingredient.

EXAMPLE H

Ampoules

A solution of 1 kg of an active ingredient according to the invention in 60 l of bidistilled water is sterile filtered, transferred into ampoules, lyophilised under sterile conditions and sealed under sterile conditions. Each ampoule contains 10 mg of active ingredient.

The invention claimed is:

1. A compound selected from:

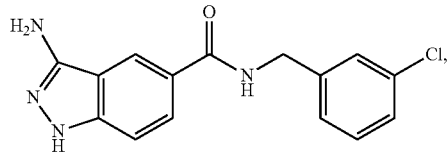

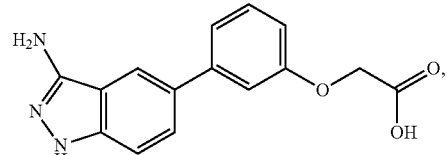

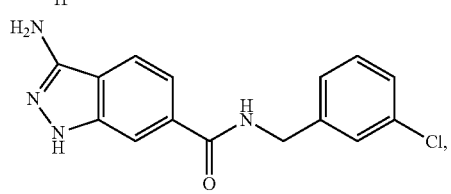

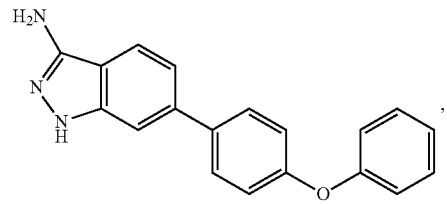

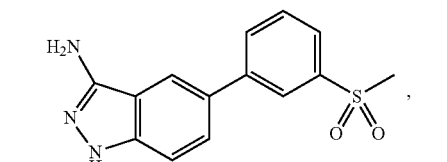

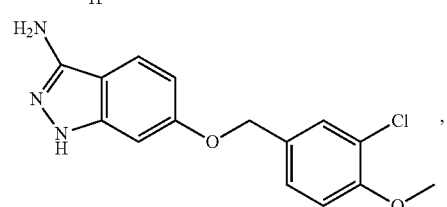

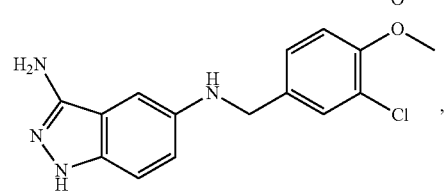

-continued
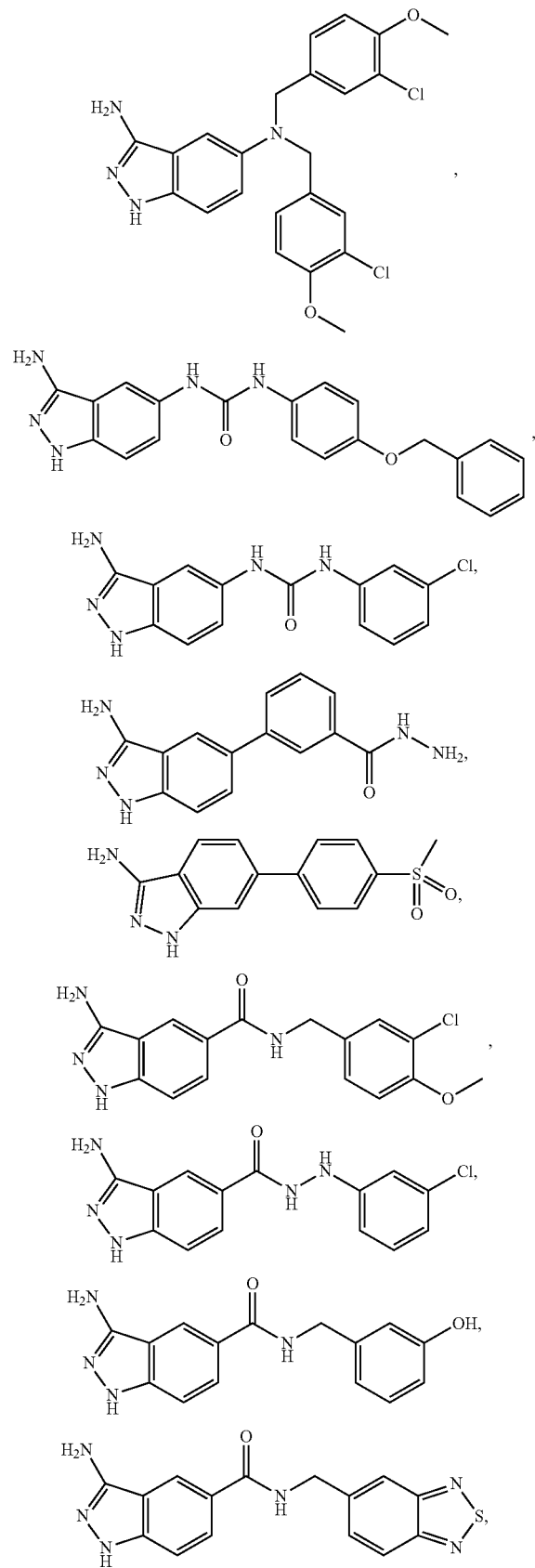
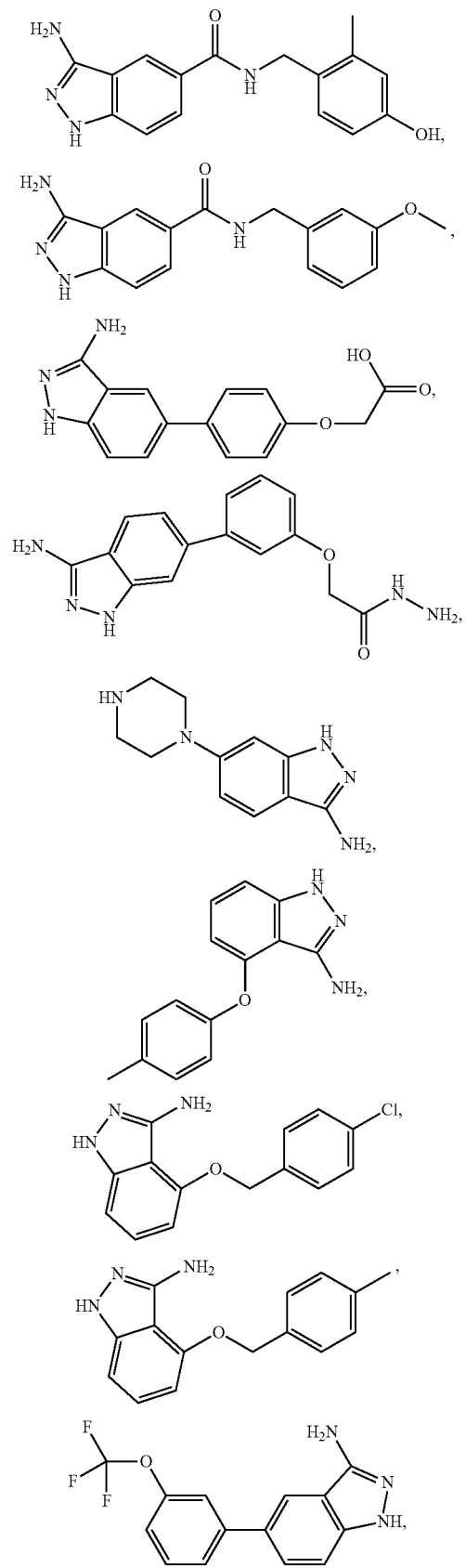

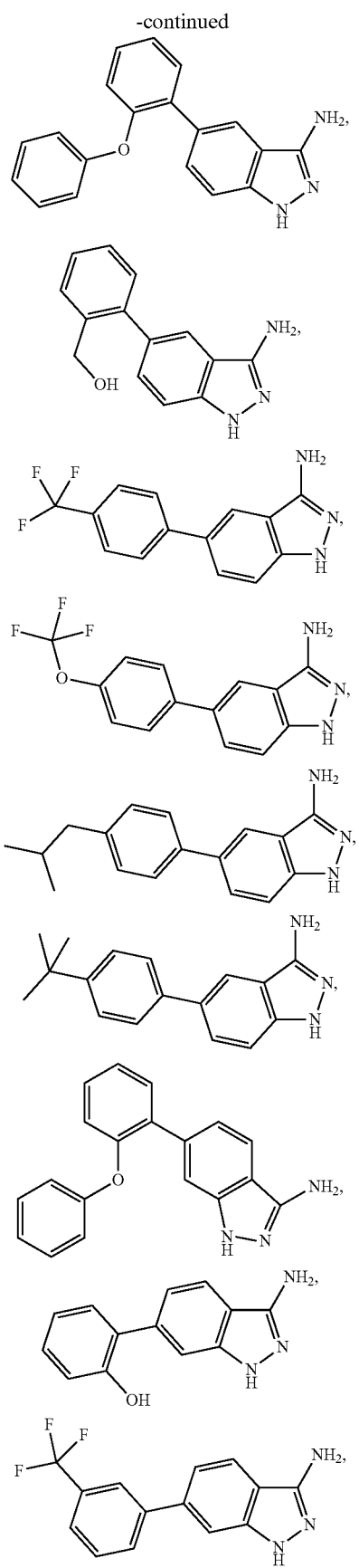
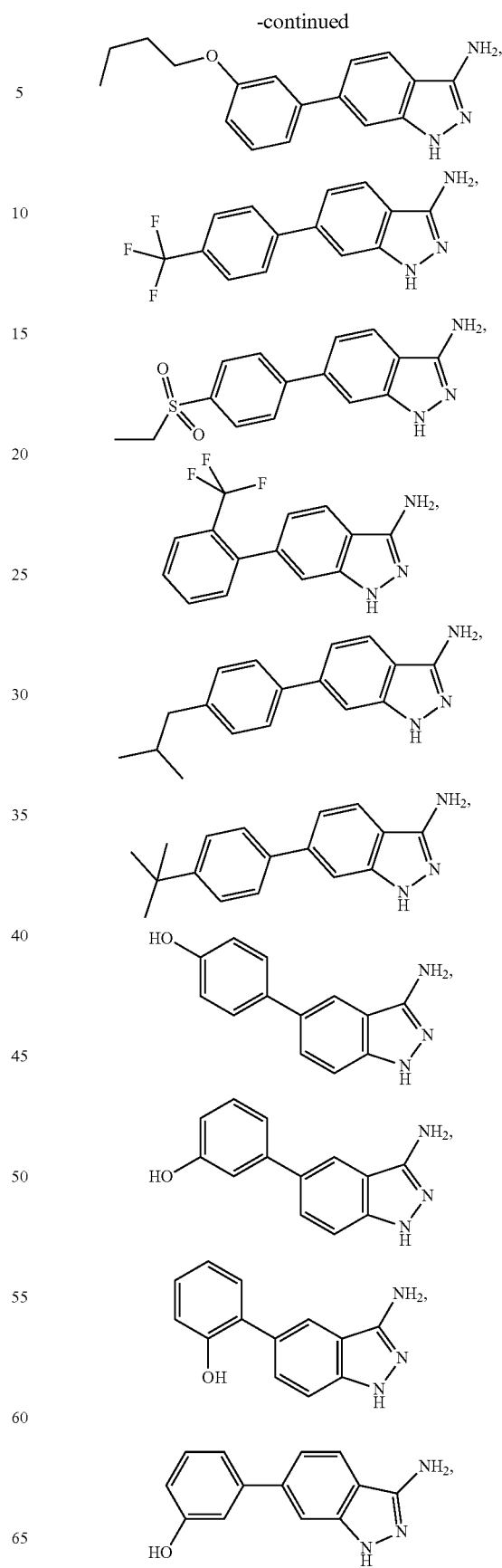

-continued

-continued
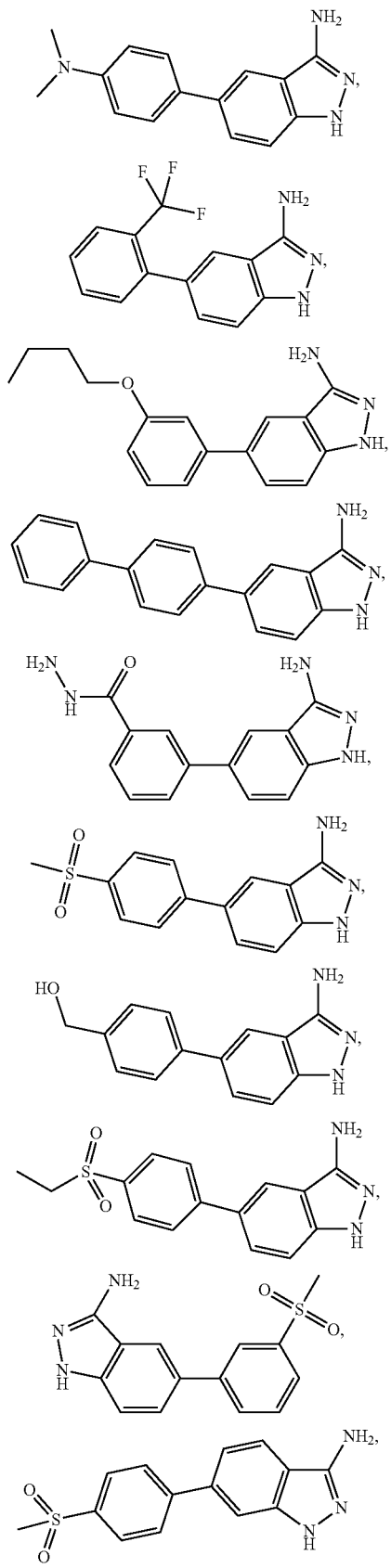
-continued
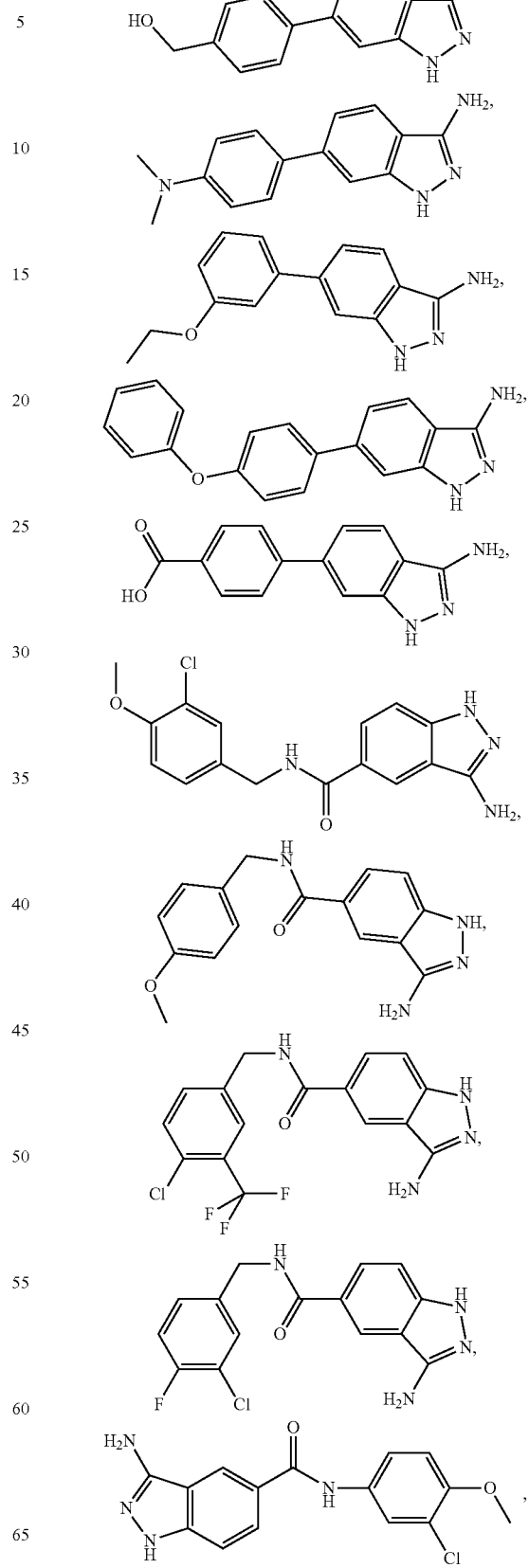

-continued

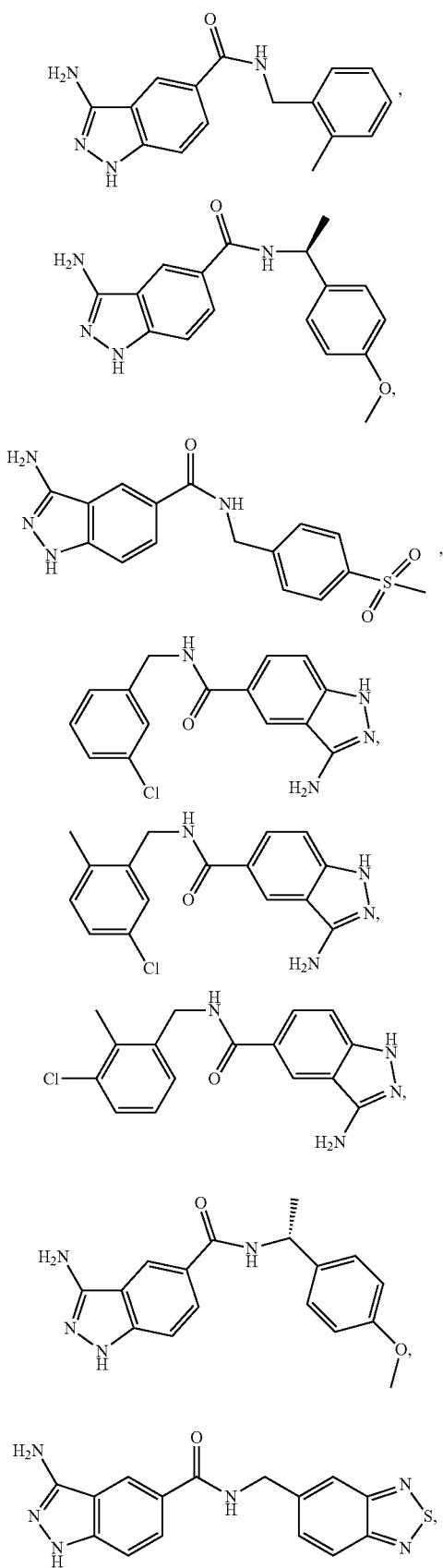
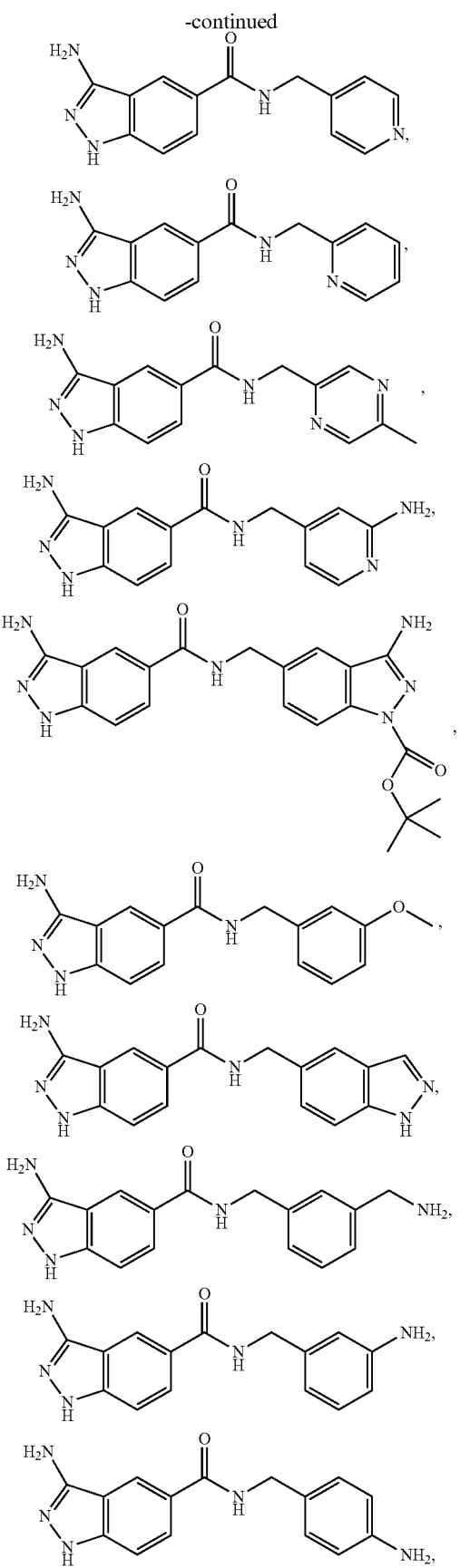

-continued
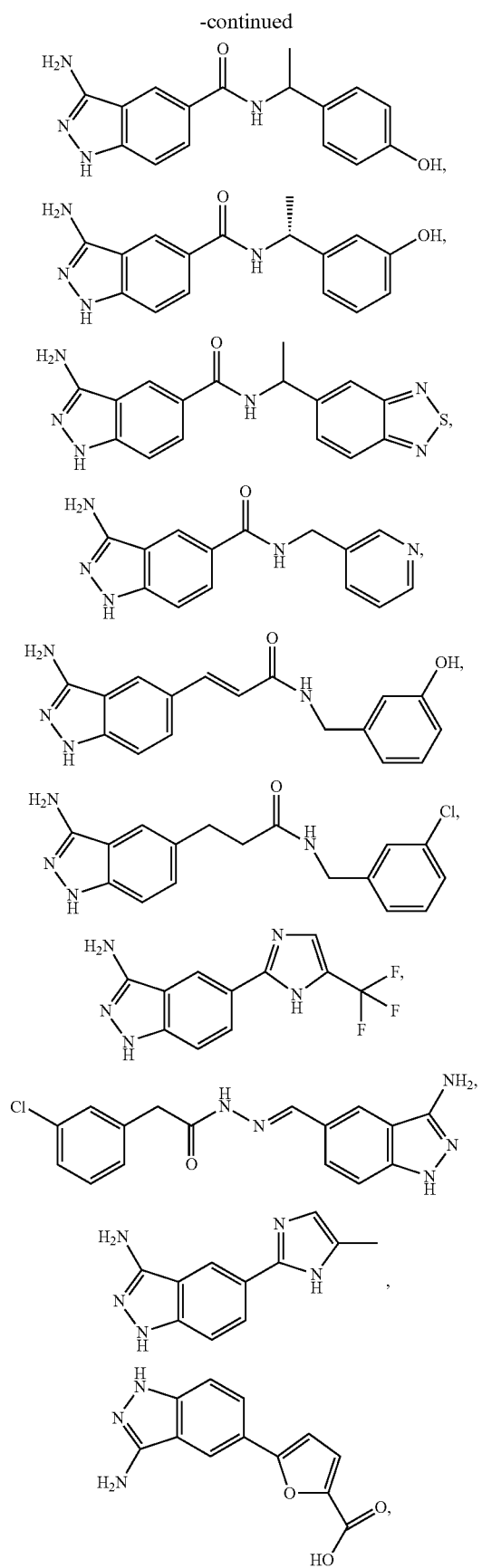
-continued
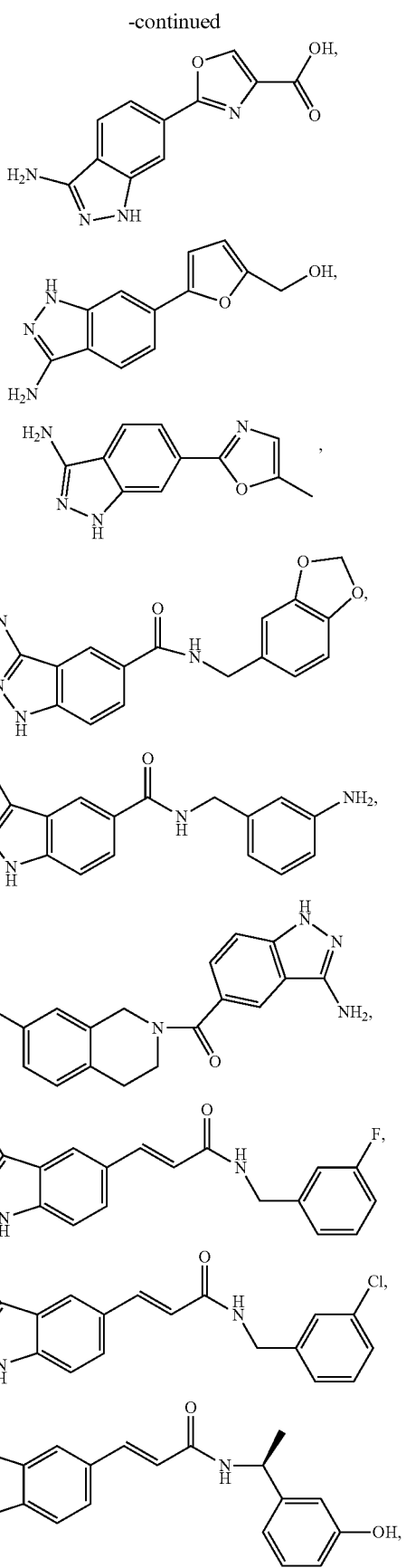

-continued
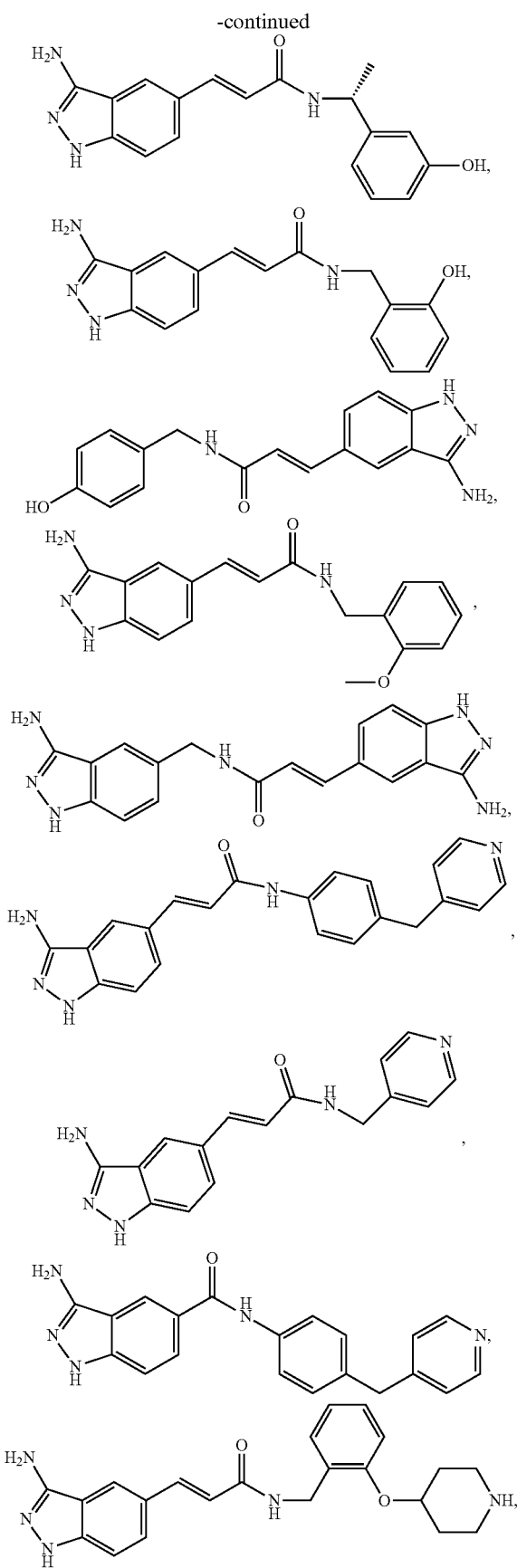
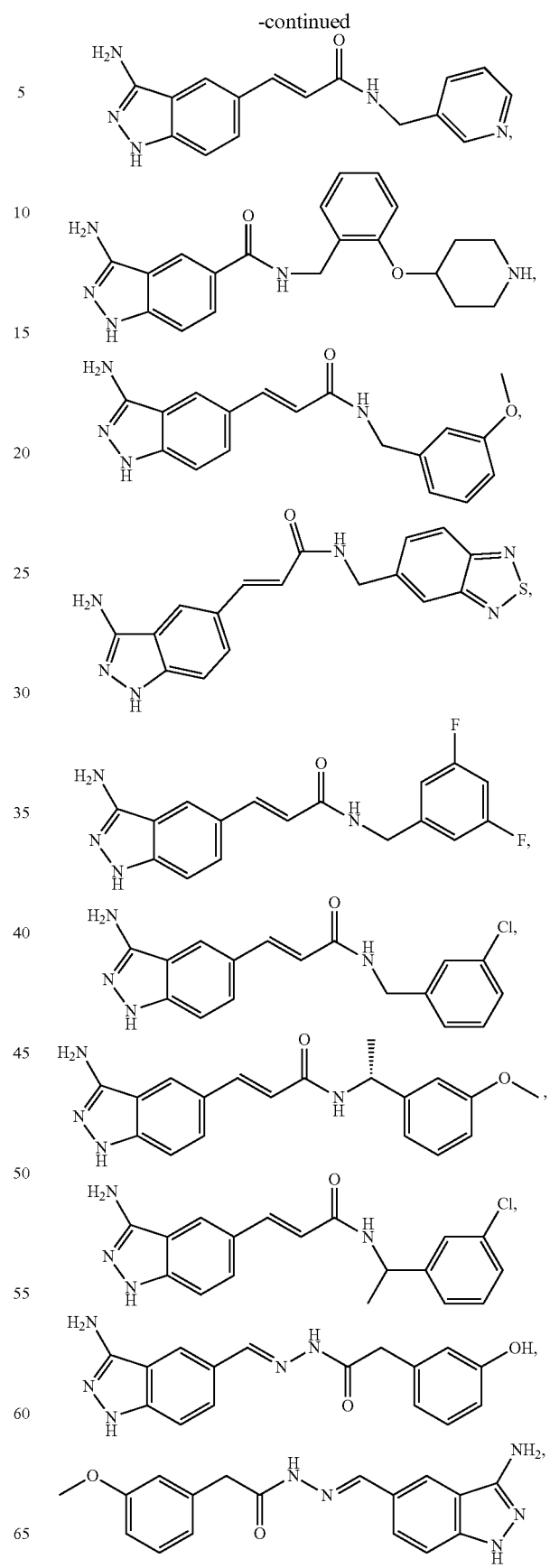

-continued

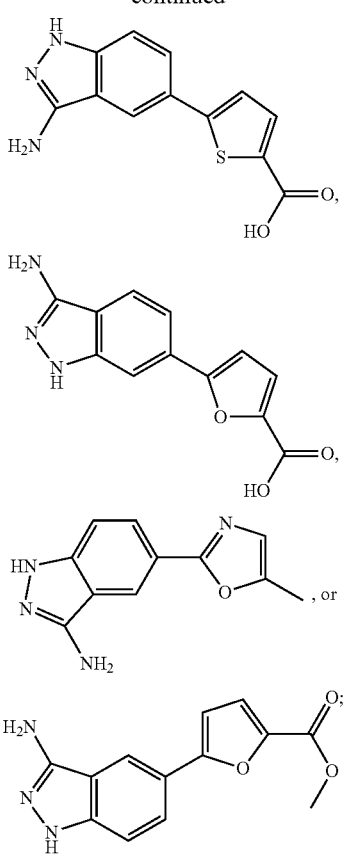

and pharmaceutically acceptable salts and stereoisomers thereof, including mixtures thereof in all ratios.

2. A process for the preparation of a compound according to claim 1, said process comprising:

a) for the preparation of a compound wherein
W is i) —[C(R$^3$)$_2$]$_n$CONH[C(R$^3$)$_2$]$_n$— or
ii) —[C(R$^3$)$_2$]$_n$CONHNH[C(R$^3$)$_2$]$_n$—,
a compound of formula II

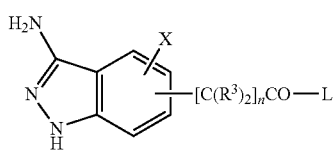

wherein L is Cl, Br, I or a free or reactively functionally modified OH group,
is reacted with
i) a compound of formula IIIa

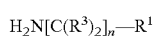 IIIa, or
ii) a compound of formula IIIb

 IIIb, or
b) for the preparation of a compound wherein
W is —[C(R$^3$)$_2$]$_n$NHCO[C(R$^3$)$_2$]$_n$—,
a compound of formula IV

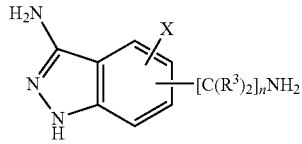 IV is reacted with a compound of formula V

L-CO—[C(R$^3$)$_2$]$_n$—R$^1$     V wherein L is Cl, Br, I or a free or reactively functionally modified OH group,
or
c) for the preparation of a compound wherein
W is —[C(R$^3$)$_2$]$_n$—, —[C(R$^3$)$_2$]$_n$O[C(R$^3$)$_2$]$_n$—, —[C(R$^3$)2]$_n$NR$^3$[C(R$^3$)$_2$]$_n$— or —[C(R$^3$)$_2$]$_n$NR$^1$[C(R$^3$)$_2$]$_n$—,
a compound of formula VI

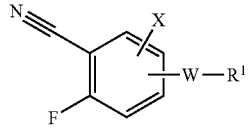 VI is reacted with hydrazine,
or
d) for the preparation of a compound wherein
W is —[C(R$^3$)$_2$]$_n$NHCONH[C(R$^3$)$_2$]$_n$—
a compound of formula IV is reacted with a compound of formula VII O=C=N—[C(R$^3$)$_2$]$_n$—R$^1$     VII, or
e) a compound of formula (I) is liberated from one of its functional derivatives by treatment with a solvolysing or hydrogenolysing agent, and/or a base or acid of formula I is converted into one of its salts.

3. A pharmaceutical composition comprising at least one compound according to claim 1 and at least one excipient and/or adjuvant.

4. A composition according to claim 3, wherein said composition further comprises at least one further medicament active ingredient.

5. The compound

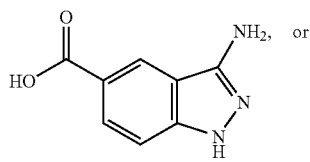

-continued
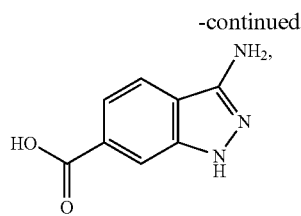
or a salt thereof.
6. A compound according to claim 1, wherein said compound is a pharmaceutically acceptable salt.
7. A compound according to claim 1, wherein said compound is selected from:
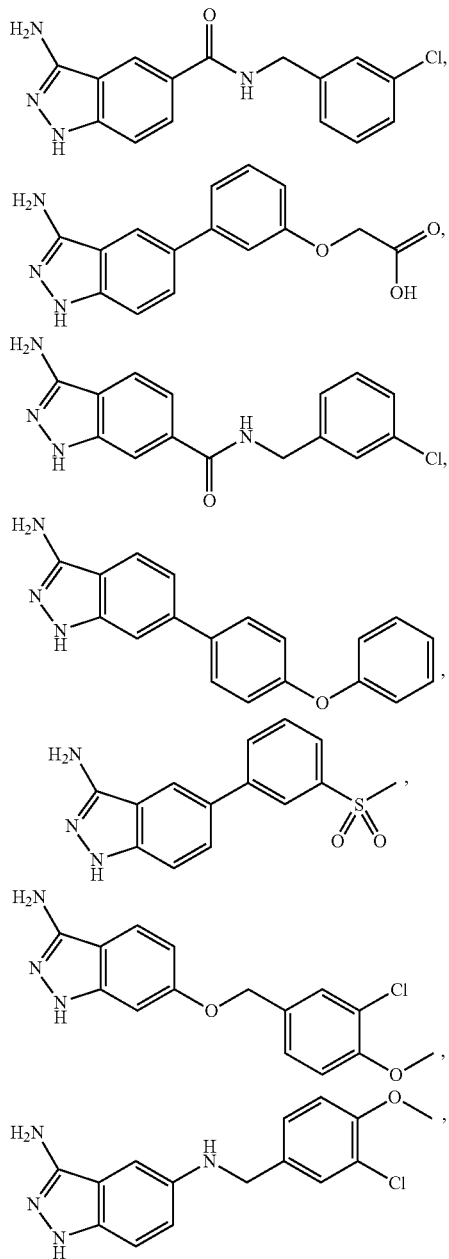
-continued
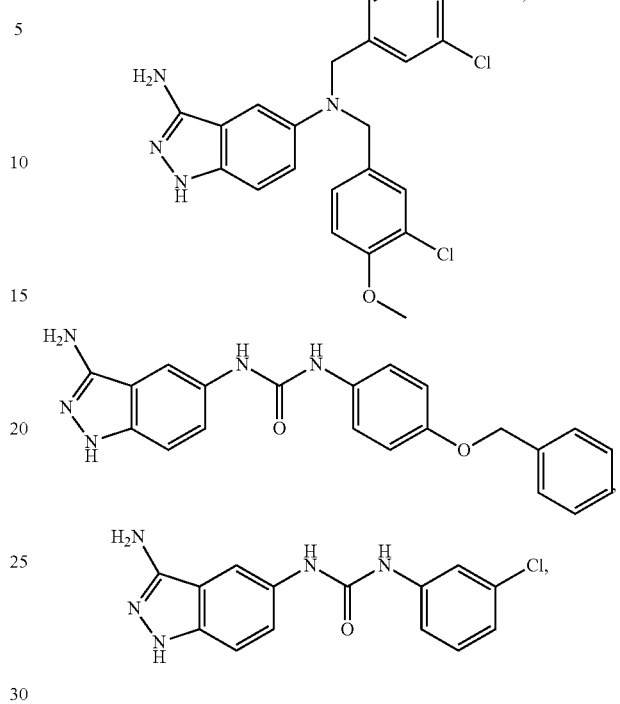
and pharmaceutically acceptable salts and stereoisomers thereof.
8. A compound according to claim 1, wherein said compound is selected from:

-continued
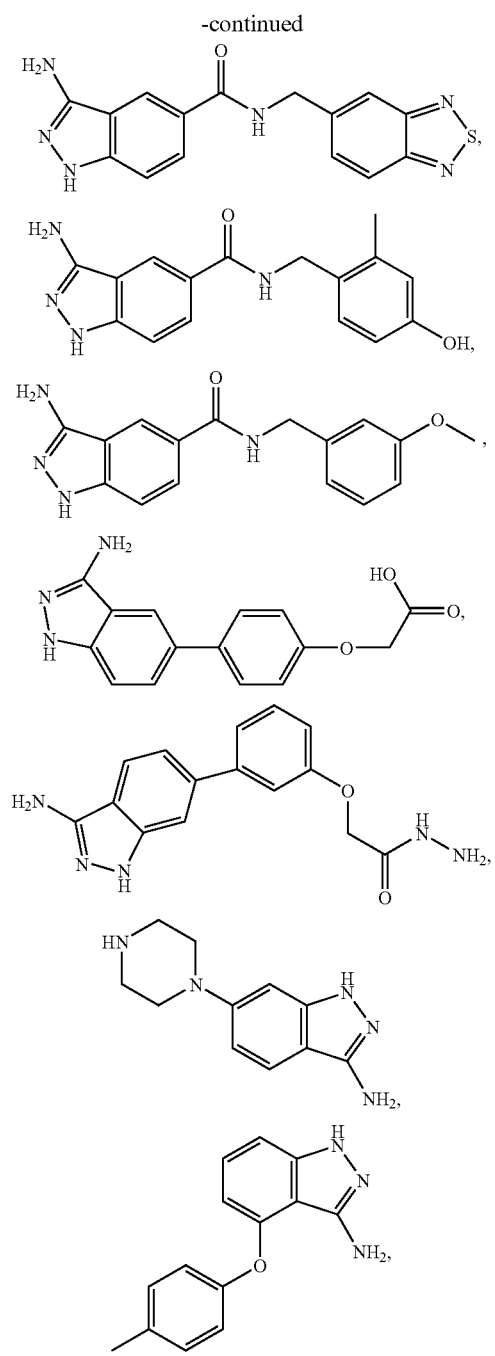
and pharmaceutically acceptable salts and stereoisomers thereof.
9. A compound according to claim 1, wherein said compound is selected from:
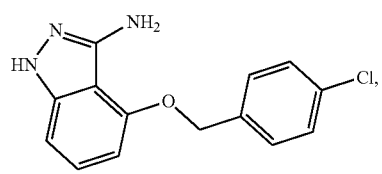
-continued
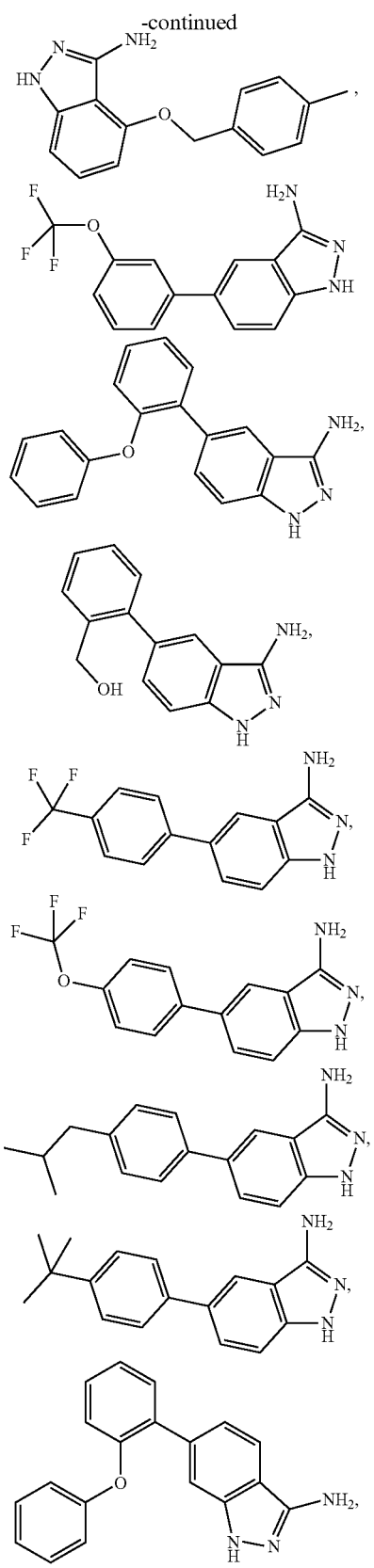
and pharmaceutically acceptable salts and stereoisomers thereof.

10. A compound according to claim 1, wherein said compound is selected from:
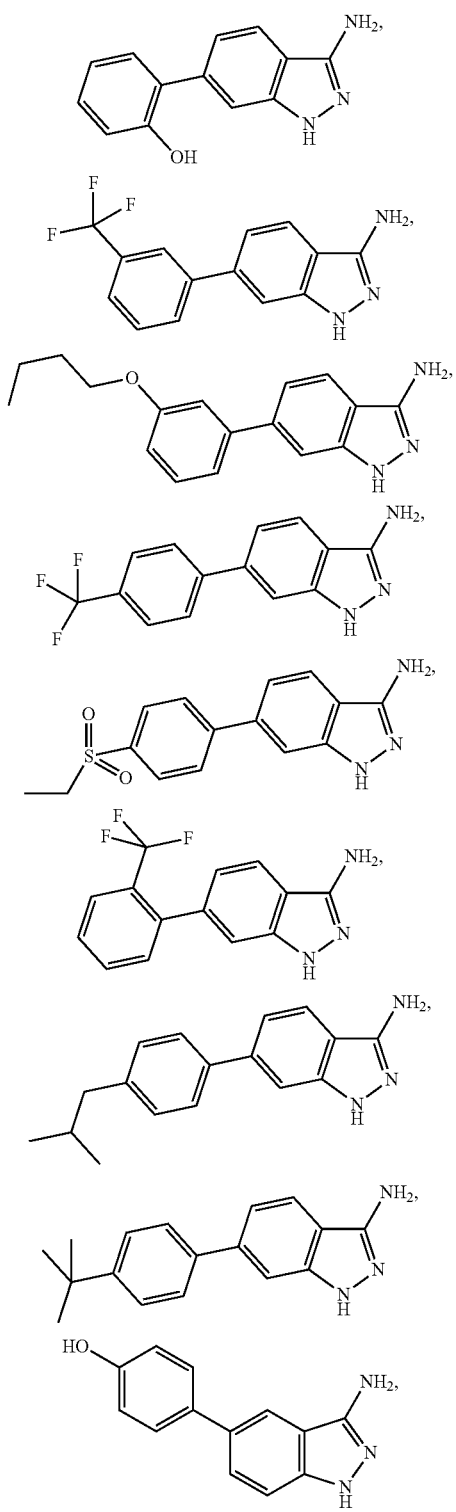
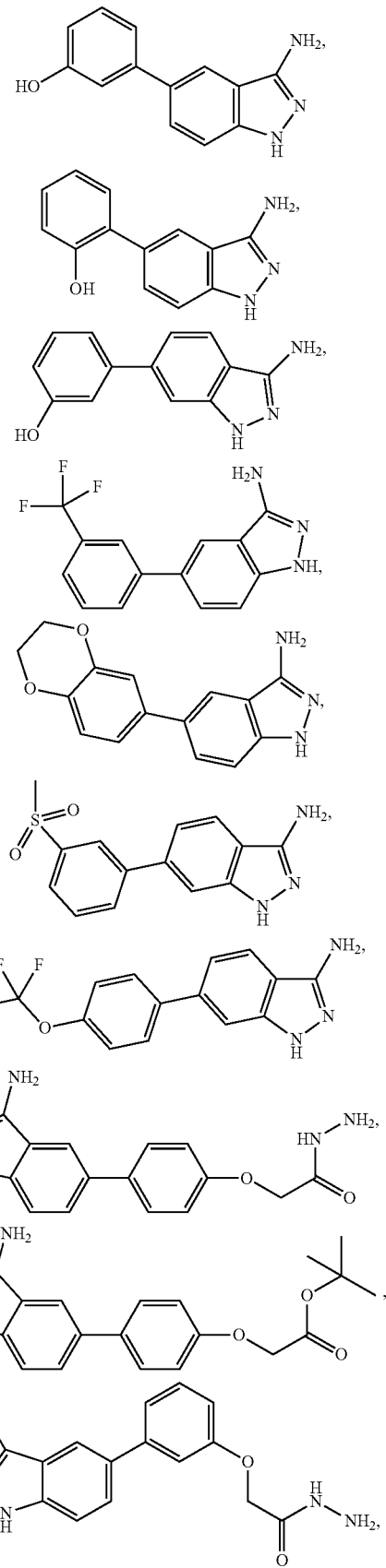
and pharmaceutically acceptable salts and stereoisomers thereof.
11. A compound according to claim 1, wherein said compound is selected from:

-continued
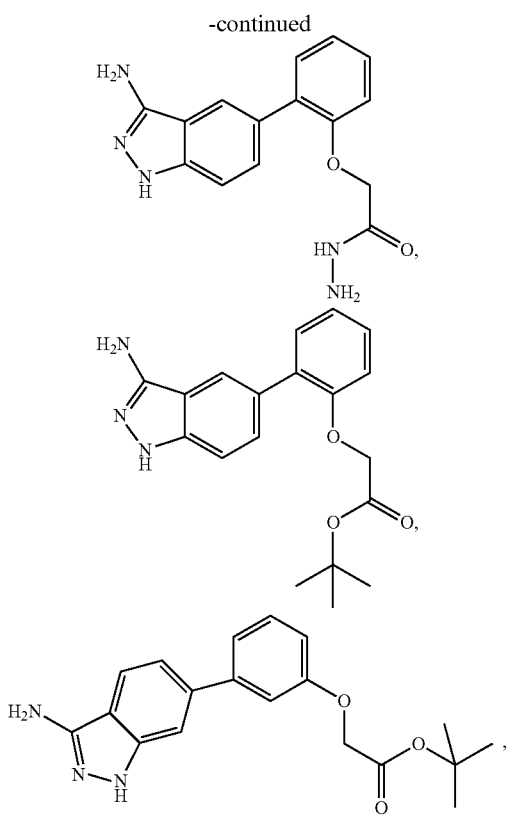
and pharmaceutically acceptable salts and stereoisomers thereof.
12. A compound according to claim 1, wherein said compound is selected from:
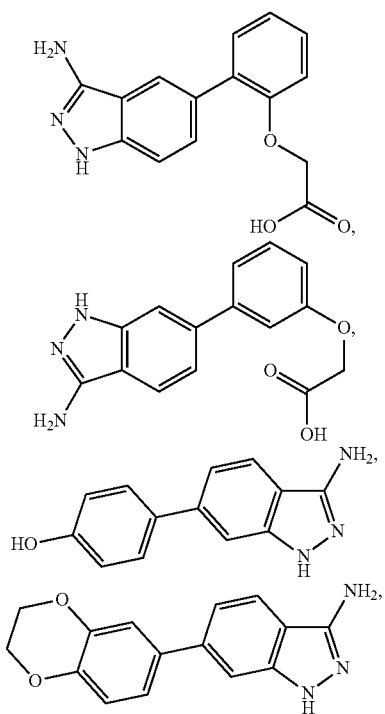
-continued
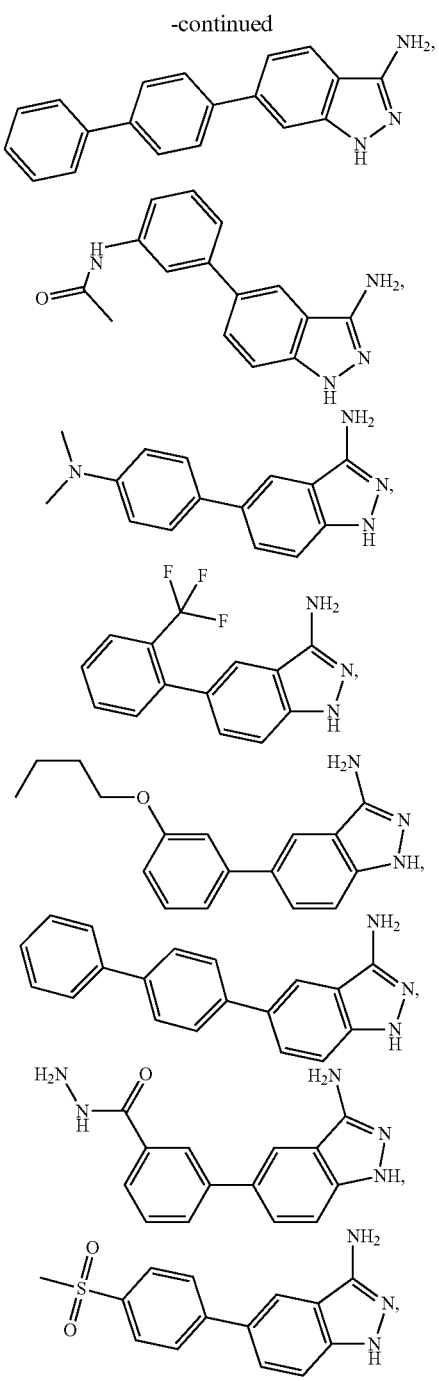
and pharmaceutically acceptable salts and stereoisomers thereof.
13. A compound according to claim 1, wherein said compound is selected from:
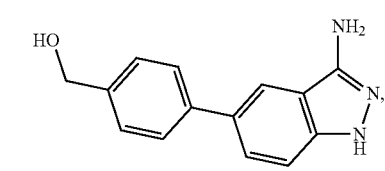

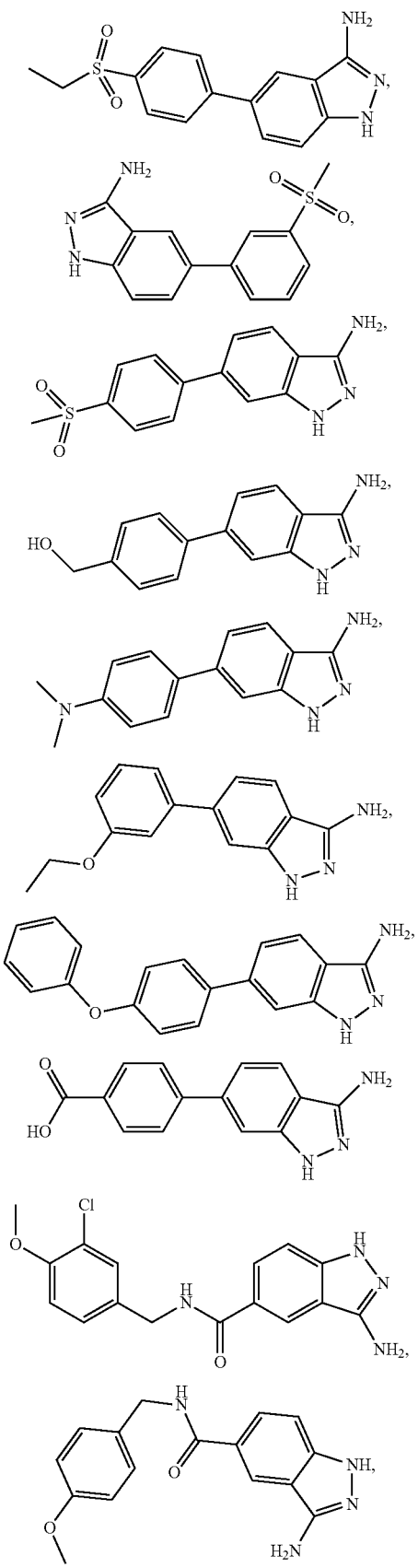
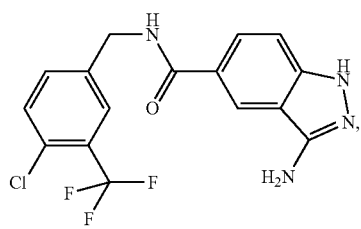
and pharmaceutically acceptable salts and stereoisomers thereof.
14. A compound according to claim 1, wherein said compound is selected from:
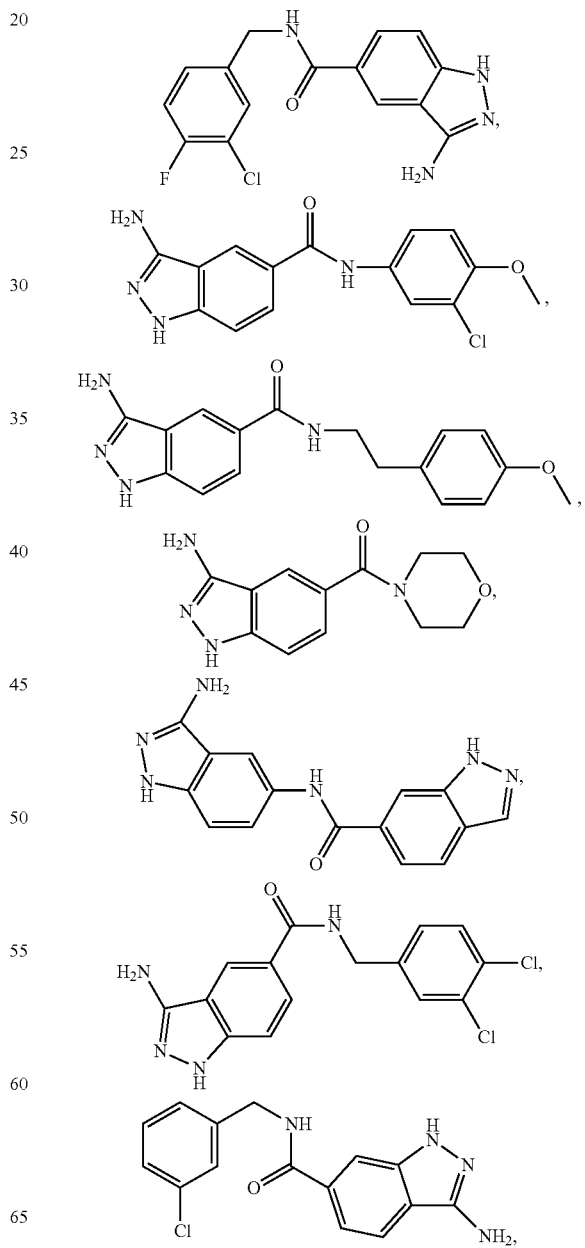

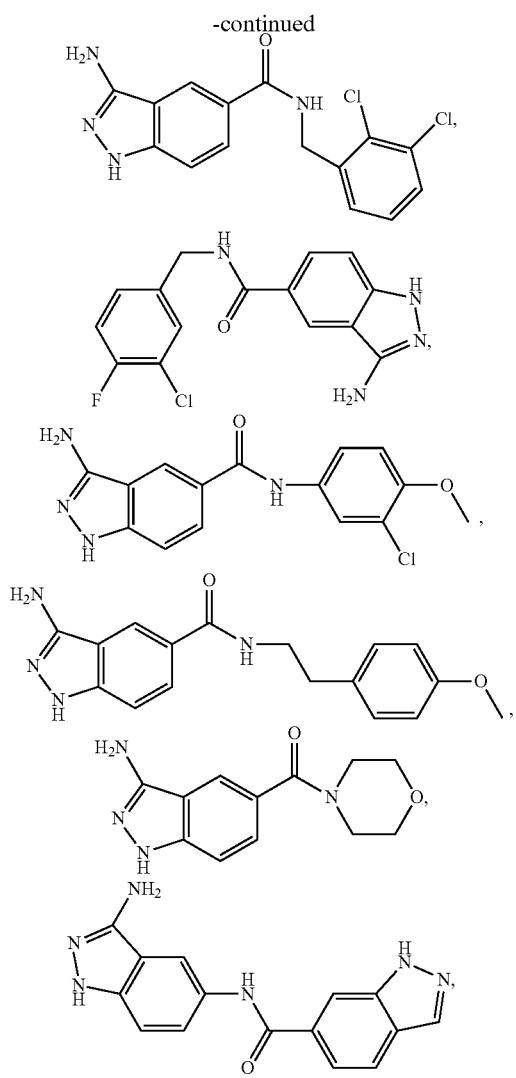
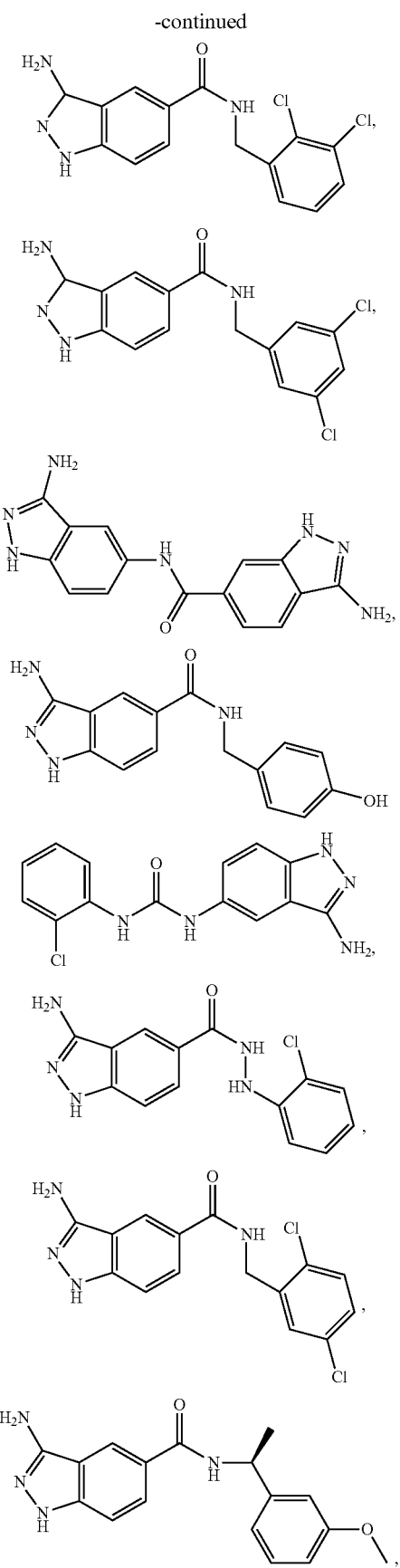
and pharmaceutically acceptable salts and stereoisomers thereof.
15. A compound according to claim 1, wherein said compound is selected from:
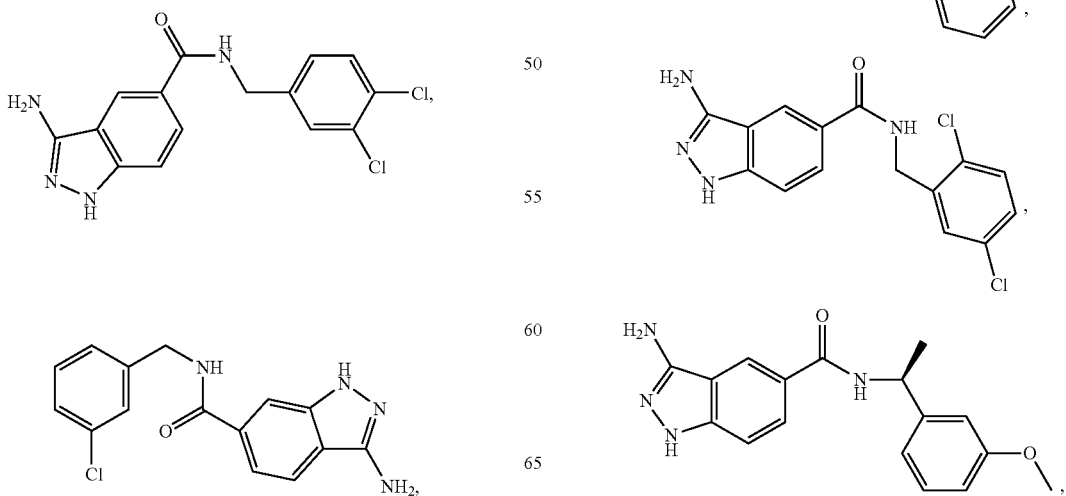

-continued
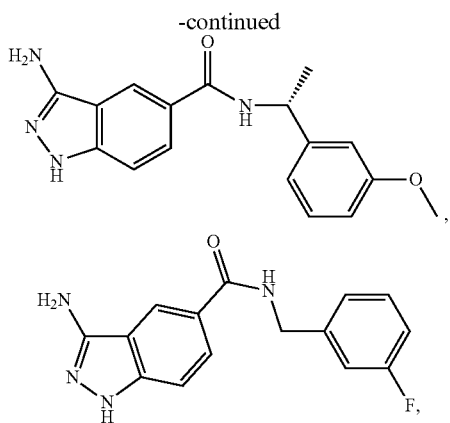
and pharmaceutically acceptable salts and stereoisomers thereof.
16. A compound according to claim 1, wherein said compound is selected from:
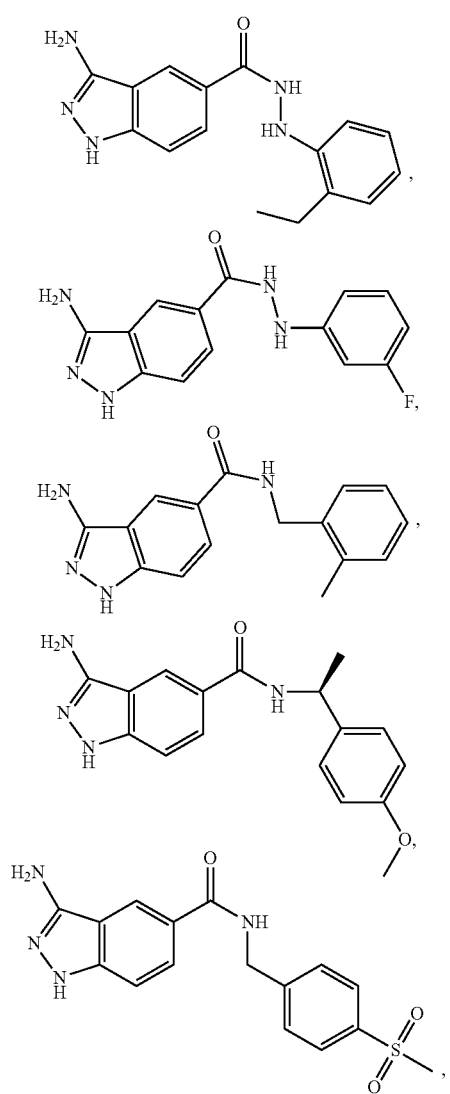
-continued
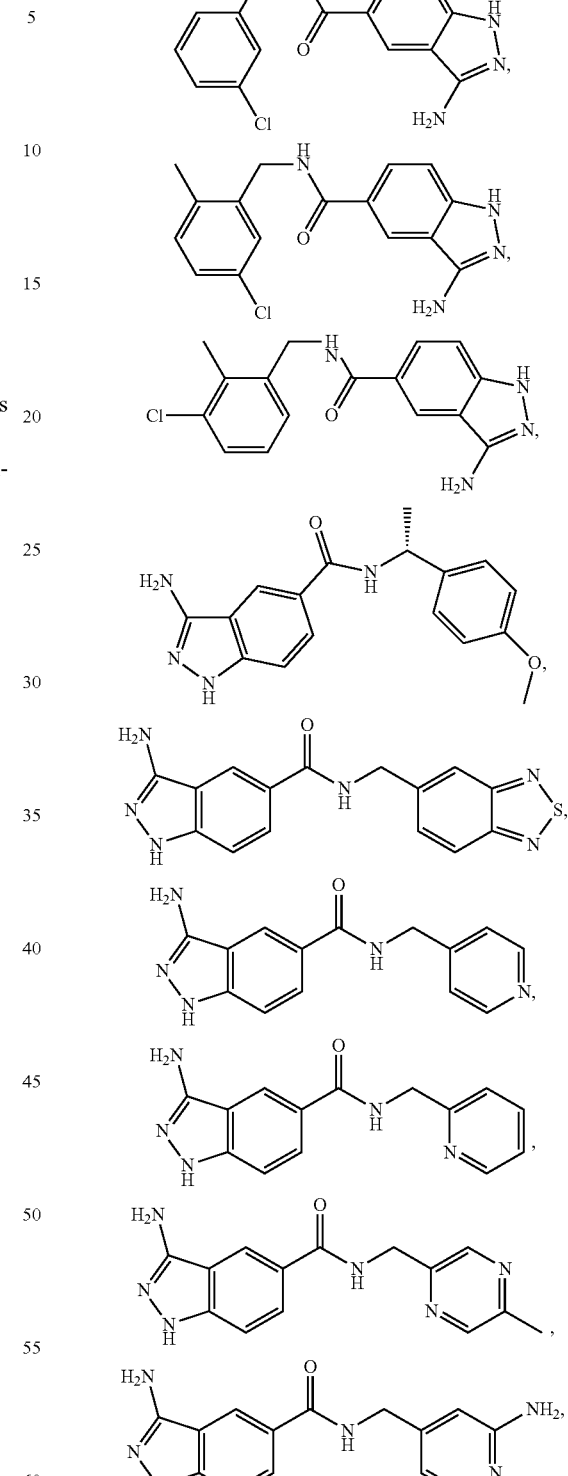
and pharmaceutically acceptable salts and stereoisomers thereof.
17. A compound according to claim 1, wherein said compound is selected from:

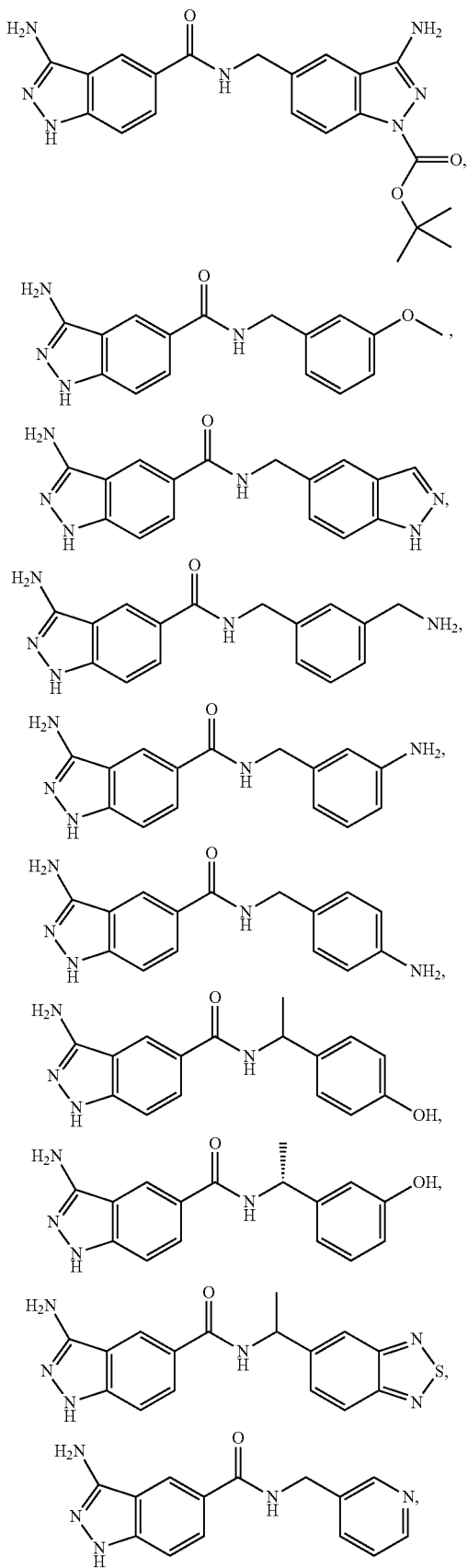
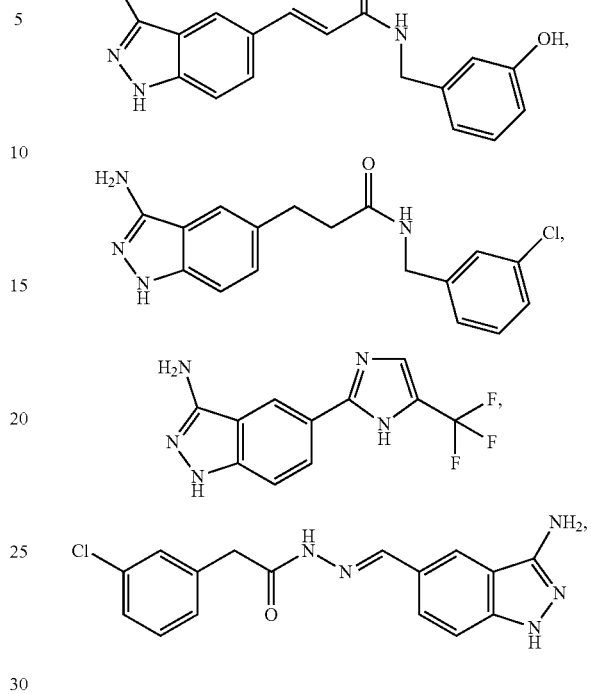
-continued
and pharmaceutically acceptable salts and stereoisomers thereof.
18. A compound according to claim 1, wherein said compound is selected from:
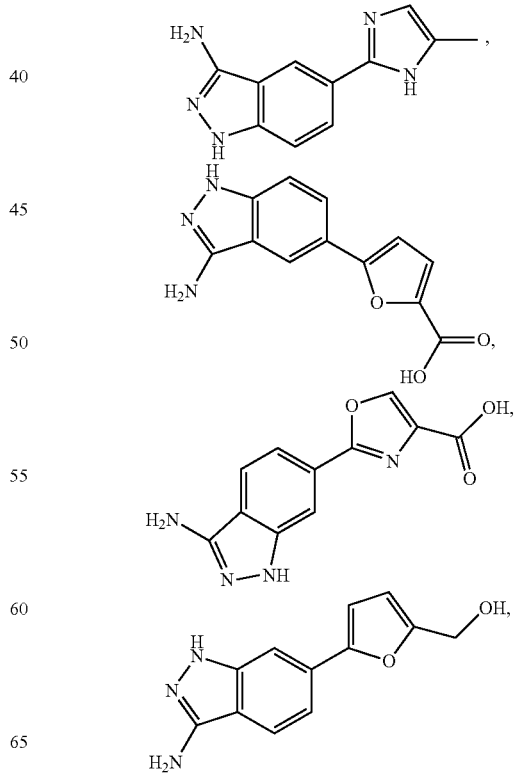

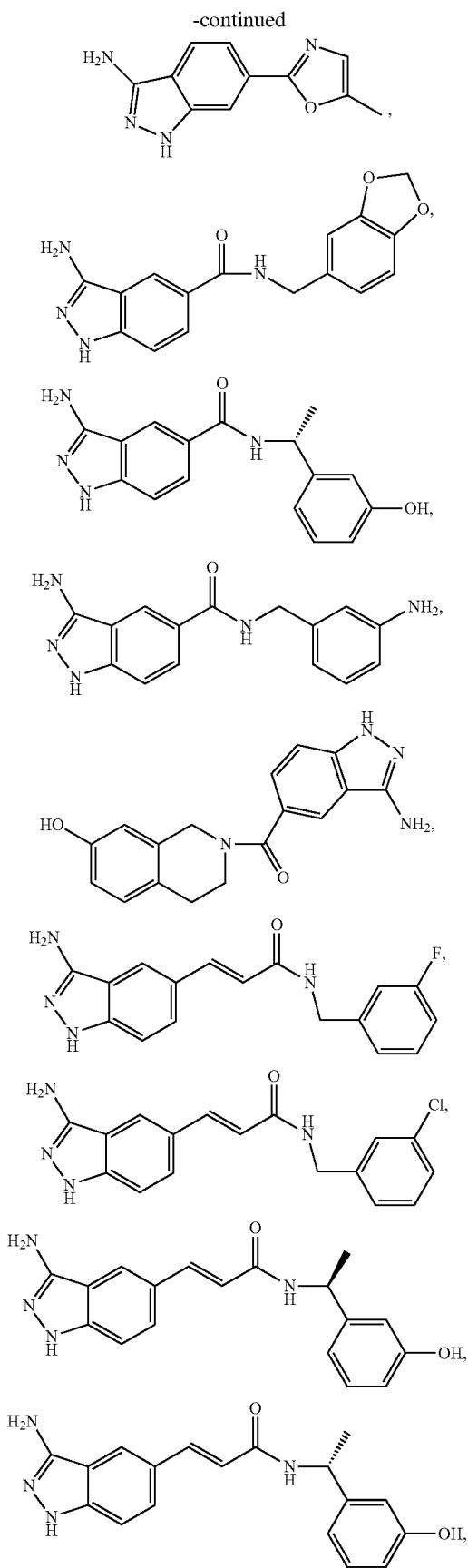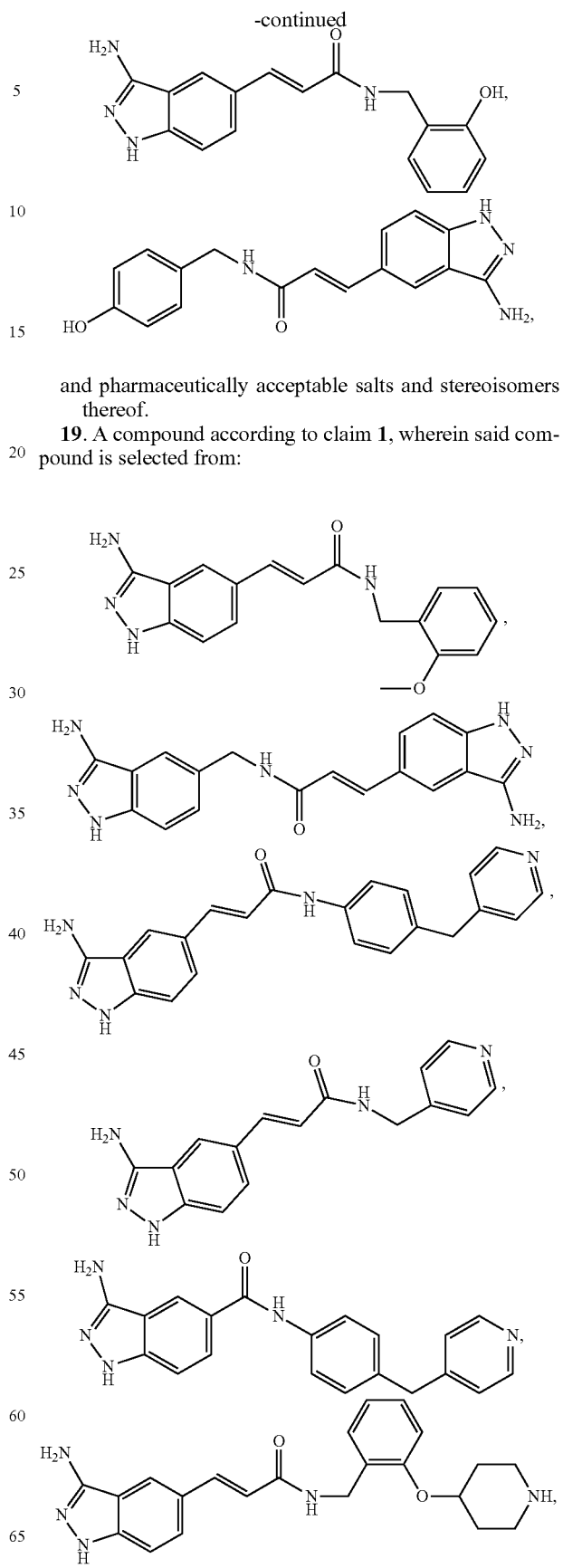
and pharmaceutically acceptable salts and stereoisomers thereof.
19. A compound according to claim 1, wherein said compound is selected from:

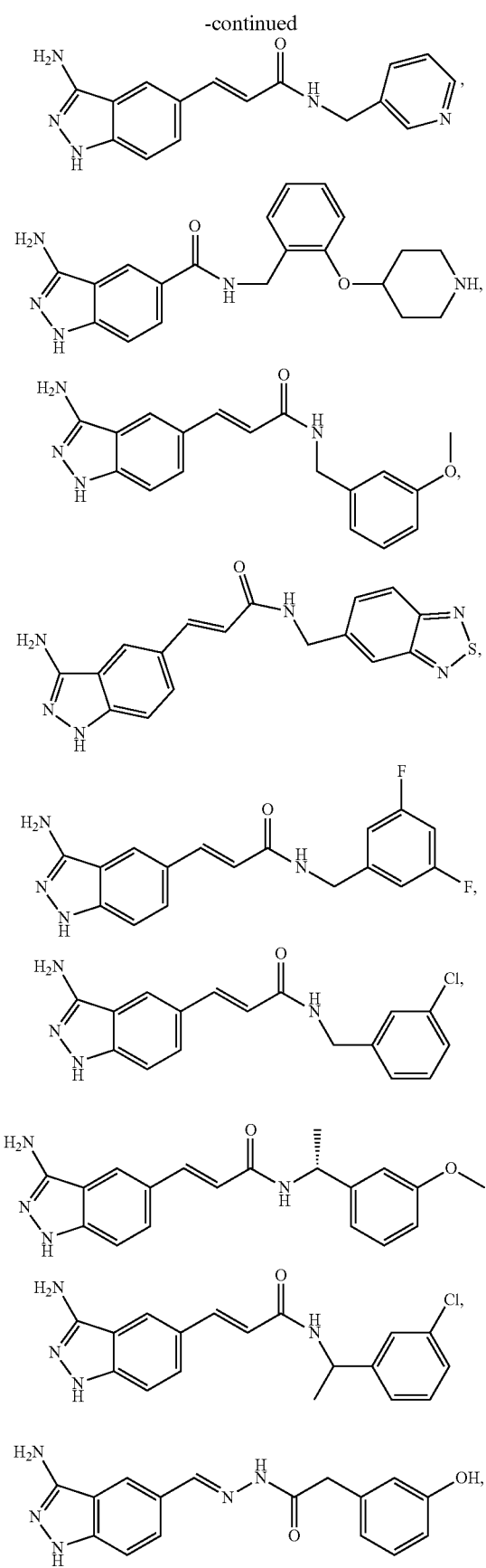
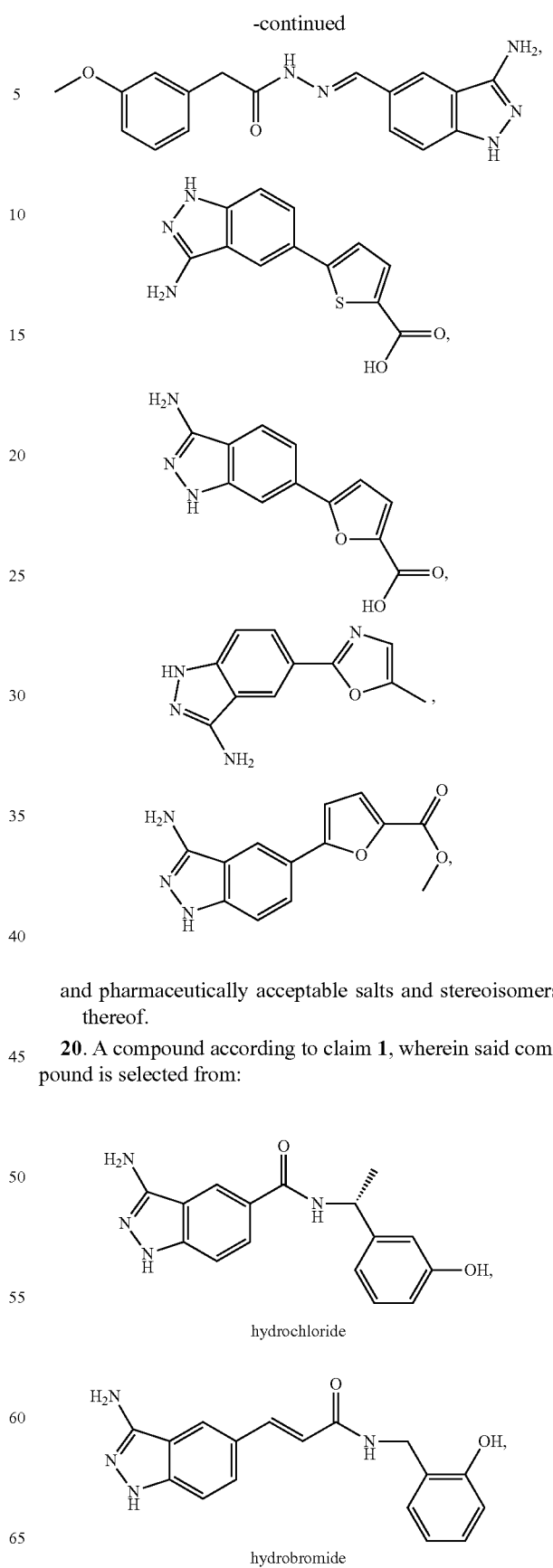
and pharmaceutically acceptable salts and stereoisomers thereof.
20. A compound according to claim 1, wherein said compound is selected from:

-continued
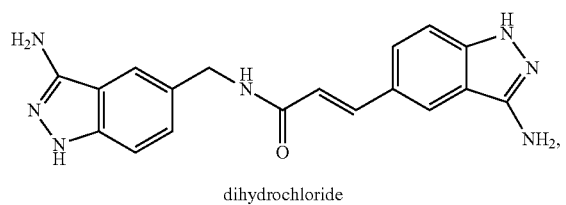
dihydrochloride
dihydrochloride
-continued
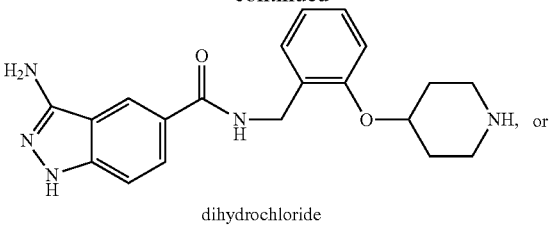
dihydrochloride
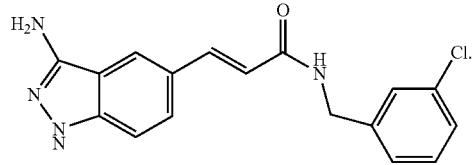
hydrochloride
* * * * *